US008449744B2

(12) United States Patent
Nissum

(10) Patent No.: US 8,449,744 B2
(45) Date of Patent: May 28, 2013

(54) MS-COMPATIBLE NONIONIC OR ZWITTERIONIC SURFACTANTS IN FREE-FLOW ELECTROPHORESIS

(75) Inventor: Mikkel Nissum, Poing (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 295 days.

(21) Appl. No.: 12/742,306

(22) PCT Filed: Nov. 12, 2008

(86) PCT No.: PCT/EP2008/065405
§ 371 (c)(1),
(2), (4) Date: Dec. 16, 2010

(87) PCT Pub. No.: WO2009/062967
PCT Pub. Date: May 22, 2009

(65) Prior Publication Data
US 2011/0097718 A1 Apr. 28, 2011

Related U.S. Application Data

(60) Provisional application No. 60/987,235, filed on Nov. 12, 2007.

(51) Int. Cl.
*G01N 27/447* (2006.01)
(52) U.S. Cl.
USPC ............ 204/450; 204/548; 204/644; 204/600
(58) Field of Classification Search
USPC .................. 204/450, 600, 644, 549, 548, 645
See application file for complete search history.

(56) References Cited

U.S. PATENT DOCUMENTS

| | | | |
|---|---|---|---|
| 5,275,706 | A | 1/1994 | Weber |
| 5,447,612 | A | 9/1995 | Bier et al. |
| 6,328,868 | B1 | 12/2001 | Weber |
| 2004/0010126 | A1 | 1/2004 | Lubman et al. |
| 2004/0026251 | A1 | 2/2004 | Weber |
| 2004/0045826 | A1 | 3/2004 | Weber |
| 2004/0050697 | A1 | 3/2004 | Eckerskorn et al. |
| 2004/0050698 | A1 | 3/2004 | Eckerskorn et al. |
| 2004/0101973 | A1 | 5/2004 | Weber |
| 2006/0240562 | A1 | 10/2006 | Caprioli et al. |
| 2006/0292607 | A1 | 12/2006 | Caprioli |

FOREIGN PATENT DOCUMENTS

| | | |
|---|---|---|
| EP | 1 320 747 A2 | 3/2002 |
| WO | 02/097393 A2 | 12/2002 |
| WO | 2006/047614 A2 | 5/2006 |
| WO | 2007/147862 A1 | 12/2007 |
| WO | 2008/025806 A1 | 3/2008 |

OTHER PUBLICATIONS

Holzenberg et al. "Rapid Isolation of OmpF Porin-LPS Complexes Suitable for Structure-Function Studies," Biochemistry 1989, 28, 4187-4193.*

(Continued)

*Primary Examiner* — Alex Noguerola
(74) *Attorney, Agent, or Firm* — The Webb Law Firm

(57) ABSTRACT

The invention relates to the use of MS compatible surfactants in free-flow electrophoretic methods, which allow the separation of analytes with differentiated electrophoretic mobility. The surfactant is preferably a cleavable surfactant, such as PPS.

29 Claims, 9 Drawing Sheets

OTHER PUBLICATIONS van Rooij et al. Determination of Block Length Distributions of Poly(oxypropylene) and Poly(oxyethylene) Block Copolymers by MALDI-FTICR Mass Spectrometry, Anal. Chem. 1998, 70, 843-850.*

Moritz et al. "Liquid-based free-flow electrophoresis-reversed-phase HPLC: a proteomic tool," Nature Methods, vol. 2, No. 11., Nov. 2005.*

Chen et al. "Optimization of Mass Spectrometry-Compatible Surfactants for Shotgun Proteomics," Journal of Proteome Research 2007, 6, 2529-2538, published on Web May 27, 2007.*

"PPS Silent Surfactant FAQ" posted by Expedeon/Protein Discovery on http://www.proteindiscovery.com/product-support/pps-silent-surfactant-faq/ , publication date unknown, downloaded Nov. 15, 2012.*

Leite et al. "Removal of monovalent cation adducts using a matrix additive during MALDI-TOF-MS analysis of peptides," posted by Invitrogen at http://www.invitrogen.com/etc/medialib/en/filelibrary/pdf.Par.86038.File.dat/TP164.pdf, publication date unknown, downloaded Nov. 15, 2012.*

Wenisch et al. "PrIME purificaiotn of *Aspergillus niger* Glucoamylase", published by Amersham Biosciences, publication date not known, downloaded from https://www.gelifesciences.com/gehcls_images/GELS/Related%20Content/Files/1314716762536/litdoc35049a_20110830184321.pdf on Nov. 15, 2012.*

Wang et al.; "Free Flow Electrophoresis Coupled with Liquid Chromatography—Mass Spectrometry for a Proteomic Study of the Human Cell Line (K562/CR3)"; J. of Chromatography A; 2004; pp. 269-278; vol. 1053; Elsevier.

Rosinke et al.; "Matrix-Assisted Laser Desorption/Ionization Mass Spectrometry (MALDI-MS) of Membrane Proteins and Non-covalent Complexes"; J. of Mass Spectrometry, 1995; pp. 1462-1468; vol. 30; John Wiley & Sons.

Bondy et al.; "Sodium Chloride in Separation Medium Enhances Cell Compatibility of Free Flow Electrophoresis"; Electrophoresis, 1995, pp. 92-97, vol. 16; VCH Verlagsgesellschaft mbH.

Norris et al.; "Mass Spectrometry of Intracellular and Membrane Proteins Using Cleavable Detergents"; Anal. Chem.; 2003; pp. 6642-6647; vol. 75; American Chemical Society.

Norris et al.; "Nonacid Cleavable Detergents Applied to MALDI Mass Spectrometry Profiling of Whole Cells"; J. of Mass Spectrometry; 2005; pp. 1319-1326; vol. 40; Wiley InterScience.

Norris et al.; "Combination Detergent/MALDI Matrix: Functional Cleavable Detergents for Mass Spectrometry"; Anal. Chem.; 2005; pp. 5036-5040; vol. 77; American Chemical Society.

* cited by examiner

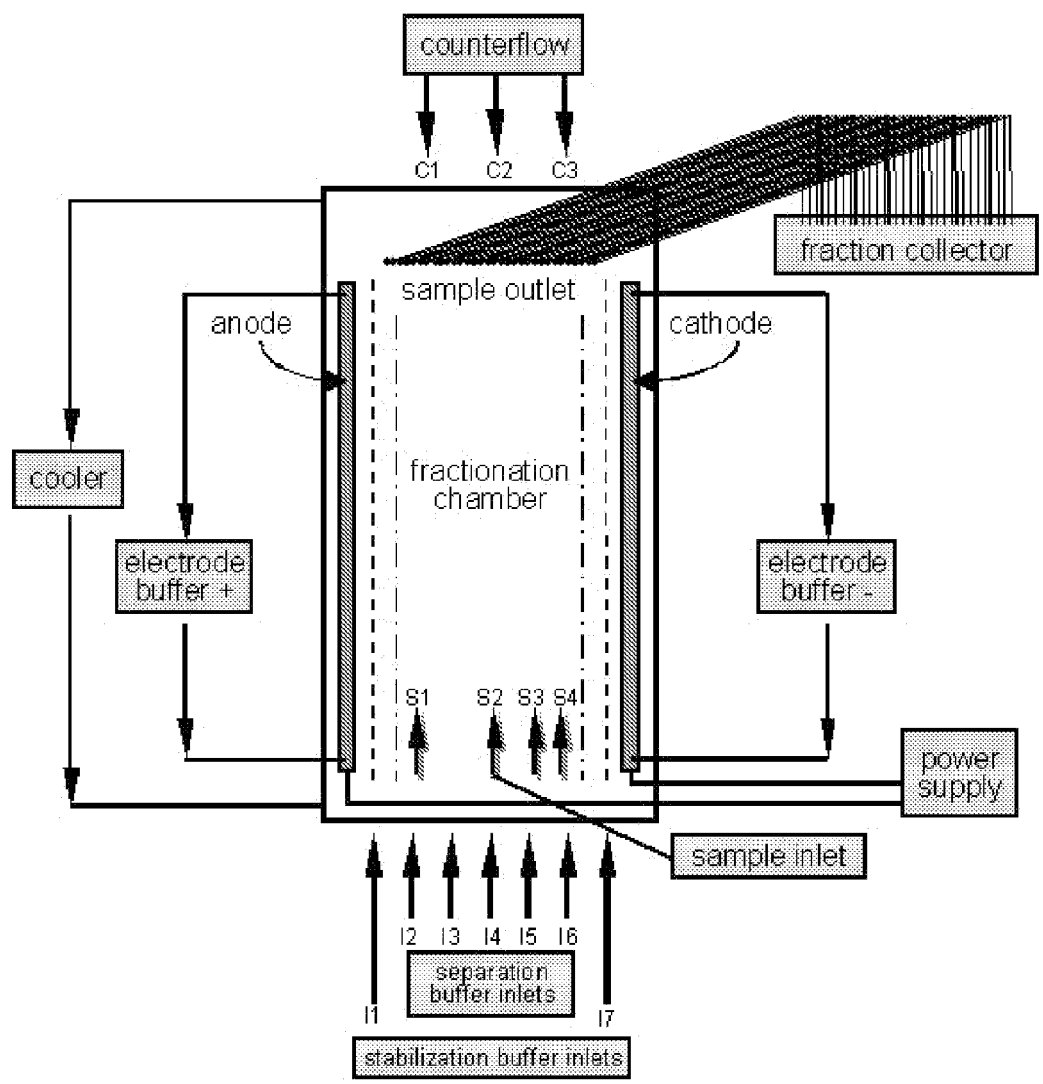
FIG: 9

MS-COMPATIBLE NONIONIC OR ZWITTERIONIC SURFACTANTS IN FREE-FLOW ELECTROPHORESIS

FIELD OF THE INVENTION

The present invention relates to methods, kits and media for carrying out efficient, selective and reproducible free-flow electrophoretic (FFE) separation of analytes, particularly samples comprising slightly soluble proteins or generally hydrophobic substances. The FFE separation according to the invention, involve the use of MS-compatible nonionic or zwitterionic surfactants.

BACKGROUND OF THE INVENTION

In order to analyze inorganic or organic molecules, especially biomolecules such as peptides, proteins, DNA, natural products, e.g., useful as drugs, metabolic intermediates, lipids and the like, it is usually required to isolate a compound of interest from a mixture prior to a downstream analysis so as to gain useful analytical data.

The isolation and subsequent analysis/characterization of, e.g., proteins, has been attempted by combining high-resolution separation techniques applied to complex protein mixtures with state-of-the-art identification methods such as mass spectrometry (MS). It is generally agreed that none of the existing separation and identification methodologies on its own can give a full account of the protein composition or the protein expression in complex mixtures, (e.g. biological matrices, biological fluids such as serum, plasma, synovial fluid, cerebrospinal fluid, urine, whole cells, cell fractions, cell lysates, or tissue extracts). This limitation, however, has not prevented the use of existing methods (or the combination of several existing technologies) to provide valuable information on a wide range of proteins, especially when either their absence or presence, or their level of expression can be correlated to a disease state.

One of the major barriers to widely applicable, e.g., MS analyses, NMR analyses, circular dichroism analyses, determination of X-ray diffraction patterns after crystallization or UV-spectroscopy analyses of biological samples is the successful purification or at least substantial enrichment of the molecules of interest to make them suitable for the subsequent analysis. A hurdle to overcome in the discovery phase of proteins or other compounds is the fact that the analytical tools used at the end of the process chain such as MS have a definite detection limit for finite amounts of proteins (or peptides derived thereof). To fully exploit the sensitivity limits and purification requirements for, e.g., peptide identification by MS, it is necessary to separate and/or enrich the protein of interest from a mixture of proteins or other bioorganic mixture.

Electrophoresis is a well-established technology for separating particles based on the migration of charged particles under the influence of a direct electric current. Several different operation modes such as isoelectric focusing (IEF), zone electrophoresis (ZE) and isotachophoresis (ITP) have been developed as variants of the above separation principle and are generally known to those of skill in the art.

Free-flow electrophoresis (FFE) is a technology wherein the separation of the analytes occurs in liquid medium in the absence of a stationary phase (or solid support material). FFE is often referred to as carrier-less deflection electrophoresis or matrix-free deflection electrophoresis.

In the field of proteomics, FFE is the technology of choice for the defined separation of complex protein samples in terms of their varying isoelectric point (pI) values. Using FFE, organic and inorganic molecules, bioparticles, biopolymers and biomolecules can be separated on the basis of their electrophoretic mobility. The corresponding principles have already been described [e.g. Bondy B. et al. (1995), "Sodium chloride in separation medium enhances cell compatibility of free-flow electrophoresis", Electrophoresis 16: 92-97].

The process of FFE has been improved in recent years, e.g., by way of stabilization media and counter-flow media. This is reflected, for example, in U.S. Pat. No. 5,275,706, the disclosure of which is hereby incorporated by reference in its entirety. According to this patent, a counter-flow medium is introduced into the separation space counter to the continuous flow direction of the bulk separation medium and sample that travels between the electrodes. Both media (separation media and counter flow media) are discharged or eluted through fractionation outlets into suitable collection devices such as a micro titer plate, resulting in a fractionation process having a low void volume. Additionally, a laminar flow of the media in the region of the fractionation outlets is maintained (i.e., with very low or no turbulence).

A particular FFE technique referred to as interval FFE is disclosed, for example, in U.S. Pat. No. 6,328,868. In this patent, the sample and separation medium are both introduced into an electrophoresis chamber, and the analytes in the sample are separated using an electrophoresis mode such as zone electrophoresis (ZE), isoelectric focusing (IEF) or isotachophoresis (ITP), and are finally expelled from the chamber through fractionation outlets. Embodiments of the '868 patent describe the separation media and sample movement to be unidirectional, traveling from the inlet end towards the outlet end of the chamber, with an effective voltage applied causing electrophoretic migration to occur while the sample and media are not being fluidically driven from the inlet end towards the outlet end, in contrast to the technique commonly used in the art wherein the sample and media pass through the apparatus while being separated in an electrical field (commonly referred to as continuous FFE).

The so-called cyclic mode or cyclic interval mode in the context of FFE as used herein has been described in International application PCT/EP2007/059010 (claiming priority from U.S. provisional applications U.S. Ser. No. 60/823,833 and U.S. Ser. No. 60/883,260), which is hereby incorporated by reference in its entirety. In sum, the cyclic interval mode is characterized by at least one, and possible multiple reversals of the bulk flow direction while the sample is being kept in the electrophoretic field between the elongated electrodes. In contrast to the static interval mode, the sample is constantly in motion thereby allowing higher field strength and thus better (or faster) separation. Additionally, by reversing the bulk flow of the sample between the elongated electrodes, the residence time of the analytes in the electrical field can be increased considerably, thereby offering increased separation time and/or higher separation efficiency and better resolution. The reversal of the bulk flow into either direction parallel to the elongated electrodes (termed a cycle) can be repeated for as often as needed in the specific situation, although practical reasons and the desire to obtain a separation in a short time will typically limit the number of cycles carried out in this mode.

A number of separation media for the separation of analytes such as bioparticles and biopolymers are known in the art. For example, the book "Free-flow Electrophoresis", published by K. Hannig and K. H. Heidrich, (ISBN 3-921956-88-9) reports a list of separation media suitable for FFE and in particular for free-flow ZE (FF-ZE).

U.S. Pat. No. 5,447,612 discloses another separation medium which is a pH buffering system for separating analytes by isoelectric focusing by forming functionally stable pre-cast narrow pH zone gradients in free solution. It employs buffering components in complementary buffer pairs.

U.S. Pending Provisional Ser. No. 60/945,246 refers to volatile buffer systems suitable for FFE. The volatile buffer systems offer the advantage that they can be easily removed subsequent to a FFE step and prior to a downstream analysis such as MS, or do not disturb a downstream analysis.

Unfortunately, a variety of proteins, which have recently come into focus of today's research, are insoluble or nearly insoluble in aqueous solutions. In those methods, wherein surfactants, e.g., sodium dodecylsulfate (SDS), urea or Triton X-100 are commonly used to prevent proteins from precipitation, e.g., during electrophoresis the surfactants must be removed prior to a subsequent analysis such as MS because these surfactants interfere with the sensitivity of mass spectrometry detection. In order to address this problem, classical methods to remove such disturbing substances are normally used subsequent to a successful electrophoresis and prior to, e.g., a downstream MS analysis. These extensive and often difficult cleaning and/or purification procedures cause an increase in the overall length of time for the analysis and typically result in a loss of sample. Furthermore, these laborious procedures represent an obstacle for automation. Therefore, sample preparation is one critical, and often technically challenging task in a successful biomolecule analysis project today. There is a need for surfactants which allow a separation of (an) analyte(s) of interest from a mixture of analytes without the need of extensive time and sample consuming purification steps to remove said surfactants after the separation step. There are surfactants known in the art which are essentially suitable for mass spectrometric analysis. Non-ionic surfactants such as octyl-β-glucopyranoside have been used for mass spectrometric applications (e.g., Hatt, P et al., 1997). However, the electrophoretic separation still requires SDS and a time consuming surfactant exchange step is needed.

Norris et al. (Anal Chem. 75(23), 6642-7, 2003) describe the properties of an acid labile "cleavable detergent" named 3-[3-(bisalkyloxyethyl)pyridine-1-yl]propane-1-sulfonate (PPS) and the use of the compound during extraction of proteins and in MS analysis, but the analysis was carried out with the crude extract without a separation method to provide a separated or at least partially substantially analyte of interest.

In 2005, Norris et al. (J. Mass Spectrom., 1319-1326, 2005) describes further "cleavable detergents" which increase the solubility of proteins and which are photo labile or fluoride cleavable instead of acid labile. After cleavage of the detergents the moieties may precipitate and they no longer disturb MS analysis, or can be easily removed prior to MS analysis.

US patent application US 2006/0292607, related to Norris et al., describes methods for analyzing tissue from the surgical margin of resected tumor and describes the use of the cleavable detergent 3-[3-(bisalkyloxyethyl)pyridine-1-yl] propane-1-sulfonate (PPS) to extract proteins contained within the interior of a cell and a subsequent MS analysis thereof.

A second publication of Norris et al. in 2005 (Anal. Chem., 77, 5036-5040, 2005) is directed to the use of cleavable detergents in mass spectrometry, wherein said detergents comprise a moiety which may act as an MS-matrix after cleavage of the detergent.

In US 2006/0240562 and WO 02/097393, cleavable compositions and methods employing such compositions, especially in MALDI-MS analysis of hydrophobic proteins, are described.

WO 2006/047614 describes MS-compatible solubilizers, which can increase the solubility of an analyte and the use thereof. The solubilizers are described to be suitable for LC/MS.

WO 00/70334 and WO 03/102536 describe destructible surfactants and methods of using them. The surfactants contain dioxolane or dioxane functional groups which enables the surfactant to be broken down under acidic conditions. The surfactants described herein are anionic, which makes them unattractive for FFE methods, especially for free-flow isoelectric focusing (IEF) in view of the charge added to the particles in the sample to be separated.

Ying-Qing Yu et al. (Anal. Chem., 75, 6023-6028, 2003) describe acid labile anionic surfactants for in-solution enzymatic digestion of proteins. The surfactants are suitable for HPLC-MS. Because of the anionic character of the surfactants, they are not suitable for FFE methods.

SUMMARY OF THE INVENTION

Today, there is a need in the art to have available methods which allow a separation of (an) analyte(s) of interest from a mixture of analytes without the need of extensive time and sample consuming purification steps to remove said surfactants subsequent to the separation step and prior to a downstream analysis.

It is an object of the present invention to provide methods and kits suitable for the separation of analytes that are insoluble or merely limited soluble in aqueous solutions, but avoiding the classical time and often sample consuming purification procedures to remove surfactants that would otherwise disturb a subsequent analysis. Embodiments of the present invention provide advantageous methods to separate analytes by FFE using surfactants that allow a subsequent MS-analysis of the separated analytes without the need of cleaning steps that are time consuming and that lead to sample-loss to remove disturbing surfactants.

Consequently, the embodiments of the present invention pertain to a method for separating analytes in a sample by free-flow electrophoresis, comprising the use of at least one MS-compatible zwitterionic or nonionic surfactant.

In another embodiment, the invention provides methods for analyzing analytes comprising a free-flow electrophoretic separation according to the present invention and a subsequent analysis of at least a part of a sample obtained from said free-flow electrophoretic separation.

Another aspect of the present invention relates to a separation medium comprising at least one MS-compatible zwitterionic or nonionic surfactant suitable for a free-flow electrophoretic method of the present invention.

Yet another aspect of the present invention relates to kits for carrying out a free-flow electrophoretic separation of analytes in a sample according to the present invention comprising at least one MS-compatible zwitterionic or nonionic surfactant.

Still another aspect relates to the use of an MS-compatible zwitterionic or nonionic surfactant, or an MS-compatible zwitterionic or nonionic cleavable surfactant according to the present invention in free-flow electrophoresis.

BRIEF DESCRIPTION OF THE FIGURES

FIG. 9: A schematic representation of a suitable FFE apparatus for carrying out the methods of the present invention.

DETAILED DESCRIPTION

Figure 1:
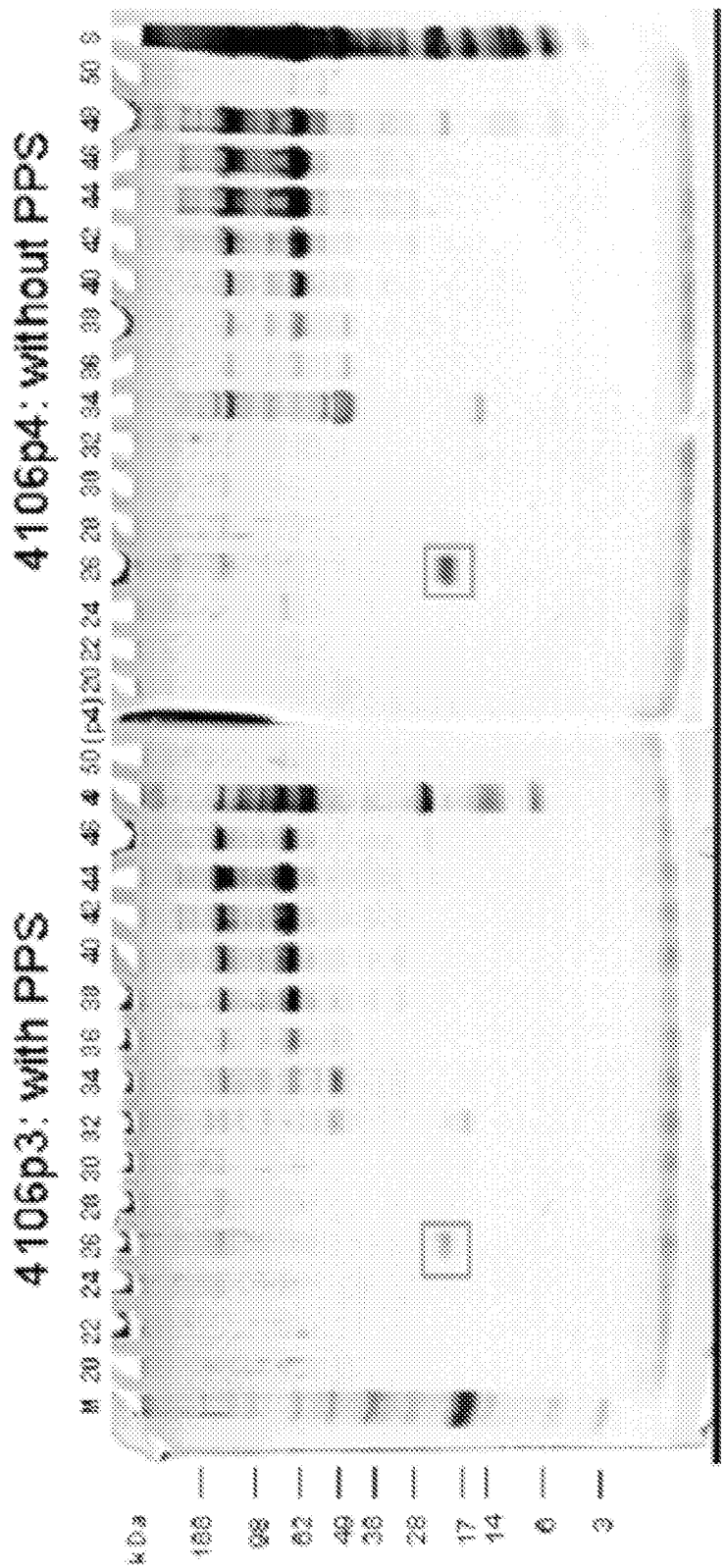
FIG. 1: Silver stained SDS-PAGE of fractions resulting from a free-flow electrophoretic separation by isoelectric focusing using a volatile buffer system of a serum sample from python sebae, wherein the separation was carried out in the presence of 3-[3-(1,1-bisalkyloxyethyl)pyridin-1-yl]propane-1-sulfonate (PPS) (first gel) and in the absence of PPS (second gel).

Embodiments of the present invention relate to methods, separation media and kits for carrying out efficient, selective and reproducible free-flow electrophoretic separations of water-soluble, slightly water-soluble and essentially water non-soluble analytes involving nonionic or zwitterionic MS-compatible surfactants, which assist in solubilizing, e.g., hydrophobic, merely slightly water-soluble or water non-soluble analytes in substantially aqueous media. Furthermore, said surfactants may be useful in samples comprising water-soluble analytes as well, since they may be necessary to prevent, e.g., precipitation of said analytes under certain conditions.

Embodiments of the present invention comprise methods with several advantages, including but not limited to one or more of the following:
 a) no time consuming and/or to sample loss leading purification steps are requested to remove disturbing surfactants between an electrophoretic separation and a subsequent analysis or an analysis wherein the MS-compatible surfactants must not disturb the analytic method;
 b) free-flow electrophoresis has a short separation time compared to gel electrophoresis and especially 2D-gel electrophoresis allowing the use of separation conditions during which a labile surfactant would otherwise be cleaved at longer residence times;
 c) the ability to modify buffer compositions during or directly subsequent to a free-flow electrophoretic separation, e.g., by counter flow media, allows an immediate stabilization or cleavage of labile surfactants; and
 d) the combination of fast separation and subsequent analysis allows a faster, a better and an automated separation and identification of analytes from a mixture of analytes.

Embodiments of the present invention may be used, for instance, to improve membrane associated protein separation, especially for proteins or analytes that are already difficult to detect in view of their low solubility and concentration in aqueous lysates.

Accordingly, one main aspect of the present invention relates to a method for separating analytes in a sample by free-flow electrophoresis, comprising performing a free-flow electrophoretic separation including at least one MS-compatible zwitterionic or nonionic surfactant.

In a preferred embodiment, at least part of the sample is collected in one or more than one fractions after the electrophoretic separation.

The advantageous methods of the present invention not only allow the separation of proteins or other compounds, but also subsequent analysis, e.g., by mass spectrometry, without the need of cleaning steps that are time consuming and that lead in sample loss to remove surfactants that disturb many downstream analyses. Optionally, if the analyte of interest is a protein, a digestion step to cut said protein into smaller peptides may be performed prior or subsequent to the free-flow electrophoresis. There is also no need to remove the MS-compatible surfactants used in the free-flow electrophoresis to perform said digestion step, the presence of said surfactants may even improve the digestion, whereas the concentration of, e.g., urea, a commonly used surfactant, has to be partially lowered or even completely removed prior to said digestion step.

Therefore, another aspect of the present invention relates to a method for analyzing analytes comprising a free-flow electrophoretic separation according to the present invention and a subsequent analysis of at least a part of a sample obtained from the free-flow electrophoresis.

In the context of the present application, the terms "to separate" and "separation" are intended to mean any spatial partitioning of a mixture of two or more analytes based on their different behavior in an electrical field. Separation therefore includes, but is not limited to, fractionation as well as to a specific and selective enrichment or depletion, concentration and/or isolation of certain fractions or analytes contained in the sample. However, it will be appreciated that fractionation is generally understood to mean a partitioning or enrichment of certain analytes within a sample from the remainder of the analytes, regardless of whether said other analytes are further separated during the electrophoresis step. It is readily apparent that there is no clear distinction between the term fractionation and separation, although the latter means a finer or more detailed spatial partitioning of the various analytes in a sample. Thus, whenever the application refers to the terms "to separate" or "separation", they are intended to include at least one of the foregoing meanings, including separation, fractionation, isolation, enrichment or depletion.

The separation may principally be carried out in a preparative manner so that certain fractions are subsequently collected, or may merely be carried out analytically, where the analyte of interest or its presence in a certain fraction is merely detected by suitable means, but not collected, e.g. for further use.

As used herein, the term "sample" refers to any composition whereof at least a part is subjected to a free-flow electrophoretic separation and/or analysis. Typically, a sample comprises, or is suspected of comprising, at least one analyte of interest.

A "fractionated sample" in the context of the present invention means a sample wherein the various analytes in the sample are separated during an FFE step and wherein the sample can thus be divided into several fractions after the FFE separation step. Those of skill in the art will understand how to collect individual fractions which exit the separation chamber of an apparatus suitable for FFE through multiple collection outlets and are generally led through individual tubings to individual collection vessels of any suitable type (e.g., 96 well plates, and sometimes plates of different sizes, e.g., 96, 384, 1536 or even more wells). It is to be understood that at least part of a sample subjected to a free-flow electrophoretic separation method is collected in one or more than one fractions after said electrophoretic separation.

The terms "analyte", "analyte of interest" and "molecule of interest" are used interchangeably herein to indicate a molecule that one wishes to separate, isolate, detect, quantify, or otherwise examine, study or analyze. Thus, the use of the term "analyte" herein is not limited to only determine the type of a molecule of interest; rather, it encompasses other observations regarding, e.g., ligand-ligand interactions, 3D structure of said molecule of interest or conformational changes, and the like. Typical analytes that can be separated by an FFE method according to embodiments of the present invention include inorganic and organic molecules, bioparticles, biopolymers and biomolecules or any combination thereof. Non limiting examples of analytes of interest, especially bioparticles, biopolymers and biomolecules, are proteins, especially membrane associated proteins, integral membrane proteins and lipophilic proteins, protein aggregates, protein complexes, peptides, hydrophobic peptides, DNA-protein complexes (e.g., chromatin), DNA, membranes, membrane fragments, lipids, saccharides and derivatives thereof, polysaccharides and derivatives thereof, hormones, liposomes, virus particles, antibodies, antibody complexes, nanoparticles or mixtures of any of the foregoing. Inorganic or organic molecules which can be separated in accordance with certain embodiments of the invention include hydrophobic polymers, such as certain constituents of plastic, latex paint particles, polystyrenes, polymethylmethacrylates, dextranes, cellulose derivatives, polyacids, pharmaceutically drugs, prodrugs, a metabolite of a drug explosives, toxins, carcinogens, poisons, allergens, infectious agents, nanoparticles and the like.

The term "protein", as used herein, refers to any protein, including without limitation peptides, enzymes, glycoproteins, hormones, receptors, antigens, antibodies, growth factors, protein complexes, protein aggregates etc., with about 20 or more amino acids. Proteins include polypeptides comprised of greater than about 20 amino acids, greater than about 50 amino acid residues, greater than about 100 amino acid residues, or greater than about 200 amino acid residues, and optionally be modified by, e.g., glycosylation, sulphation or phosphorylation.

The term "lipophilic proteins" as used herein refers to proteins having at least one lipophilic region. Membrane associated proteins, which are in vivo capable of interacting with membranes by means of van der Waals forces are a non-limiting example for lipophilic proteins. Optionally, lipophilic proteins may encompass proteins containing polar or ion groups which, e.g., interact with the polar headgroups of a membrane. Non-limiting examples are, dehydrins comprising K-segments or receptors. Receptor molecules are recognized in the art and generally have an extracellular, an intracellular and/or a transmembrane domain.

The term "integral membrane protein" as used herein relates to a protein molecule (or assembly of proteins) that in vivo is permanently attached to a biological membrane. The most common type of integral membrane proteins is the class of transmembrane proteins that span an entire biological membrane. Structurally, regions of integral membrane proteins penetrate the hydrophobic regions of the phospholipid bilayer of a membrane. Due to this interaction, integral membrane proteins can usually only be removed from the membrane by the use of surfactants that disrupt the hydrophobic interactions of the bilayer.

The terms "peptide" or "polypeptide" as used herein refer to any entity comprising at least one peptide bond, and can comprise either D and/or L amino acids. A peptide can have about 2 to about 150, preferably about 2 to about 100, more preferably about 2 to about 50 and most preferably about 2 to about 20 amino acids.

The terms "lipophobic" and "hydrophilic" may be used interchangeably herein and refer to analytes, compounds and substances that tend to dissolve in, mix with, or be wetted by water. Hydrophilic or lipophobic analytes, compounds and substances tend to be electrically charged and polar and, thus, preferring other charged and polar solvents or molecular environments.

The terms "lipophilic" and "hydrophobic" may be used interchangeably herein and refer to analytes, compounds and substances that tend to not dissolve in, mix with, or be wetted by water. Hydrophobic or lipophilic analytes, compounds and substances tend to be electrically neutral and non-polar, thus, preferring other neutral or non-polar solvents or molecular environments.

The term "a" as used herein has to be understood as "one", "at least one" or "one or more".

The terms "surfactant", "detergent", "wetting agent" and "emulsifier" may be used interchangeably herein and refer to molecules or compositions which are capable of reducing the surface tension in water. Surfactants are typically organic compounds that are amphiphilic, meaning they contain both hydrophobic groups (their "tails") and hydrophilic groups (their "heads"). Therefore, they are soluble in both organic solvents and water. For example, a surfactant promotes keeping a hydrophobic peptide or protein in an aqueous solution.

The term "MS-compatible zwitterionic or nonionic surfactant" as used herein means MS-compatible surfactants that can be zwitterionic or nonionic. In some embodiments, a zwitterionic or nonionic surfactant may be in sum negatively or positively charged depending on the pH of a distinct area between two electrodes, but a nonionic, MS-compatible surfactant is in any event not charged within the pH range, wherein an analyte of interest is inserted into and is eluted from an apparatus suitable for free-flow electrophoresis. Furthermore, it is to be understood that the isoelectric point of a zwitterionic, MS-compatible surfactant as used in the present invention is generally within the pH range of the separation zone. The term "MS-compatible surfactant" and "MS-compatible zwitterionic or nonionic surfactant" as used herein may be used interchangeably since a surfactant suitable for FFE must be either zwitterionic or nonionic within the pH range of the separation zone.

The term "zwitterionic" as used herein in the context of surfactants refers to a compound that is electrically neutral but carries formal positive and negative charges on different atoms. Examples, which are not to be understood as limiting, are, e.g., betaine derivatives, preferably sulfobetaines such as 3-(trimethylammonium)-propylsulfonat or phosphobetaines. Typically, the isoelectric point (pI) of a zwitterionic surfactant as used in the present invention is within the pH range of the separation zone, preferably the pI of a zwitterionic surfactant is within the pH range between the pH value of the sample introduction point of an apparatus and the pH value of the elution point of an analyte of interest. In some embodiments, the pI of a zwitterionic surfactant is 1.5 or less, 1 or less, 0.75 or less, 0.5 or less, or 0.25 or less pH units away from the elution pH value of an analyte of interest.

The term "nonionic" as used herein in the context of surfactants refers to (bi)polar compounds. Examples include but are not limited to saccharide derivatives having at least one hydrophobic substituent such as $C_6$, $C_7$, $C_8$, $C_9$, $C_{10}$, $C_{11}$, $C_{12-30}$-alkyl, -alkenyl, -alkynyl, -aralkyl or -aryl. Notably, acetylpyranoside and other saccharide derivatives having merely hydrophilic substituents do not belong to the group of nonionic surfactants. Typically, a nonionic surfactant is uncharged within the pH range, wherein an analyte of interest is inserted into and is eluted from an apparatus suitable for free-flow electrophoresis, preferably, a nonionic surfactant is uncharged within the pH range of the separation zone. However, depending on the pH range of said zone, it may happen that a nonionic compound nevertheless becomes charged at a certain pH outside the pH range, used to separate an analyte of interest.

The term "MS-compatible" as used herein denotes surfactants that can be used in MS analyses. The term "MS-compatible surfactants" encompasses surfactants that are per se suitable for MS analysis, i.e. without modification, and also encompasses "cleavable" surfactants which are not MS-compatible in their non-cleaved state but which can be cleaved at at least one position into at least two moieties. Said moieties can be MS-compatible or non-MS-compatible. A non MS-compatible moiety of a cleavable surfactant according to the present invention can be easily removed by, e.g., centrifugation, filtration or evaporation, whereas an MS-compatible moiety may stay in solution and may be present during a downstream analysis or may under certain conditions likewise be removed by centrifugation, filtration or evaporation. In a preferred embodiment, more than one resulting moiety is MS-compatible. Such MS-compatible cleavable surfactants are suitable, e.g., in methods comprising a protein digestion step. A protein may be insoluble in water but its fragments or part of the fragments resulting from the digest may be soluble and can be analyzed by, e.g., MS.

As a non-limiting example for the advantages provided by the cleavable surfactants of the present invention, the sensitivity of a mass spectrometric detection of an analyte in the presence of a suitable, MS-compatible surfactant is much greater than the sensitivity of a mass spectrometric detection of an analyte in the presence of, e.g., SDS. In most cases, a mass spectrum of a sample comprising SDS exhibits no signals at all or only weak signals due to an analyte treated with SDS or break down products of said analyte. In contrast, a sample that comprises said analyte and that is subjected to a mass spectrometric analysis in the presence of an MS-compatible surfactant instead of SDS exhibits signals related to the analyte and to break-down products of said analyte.

Accordingly, an MS-compatible surfactant can be understood as a surfactant whose presence in a sample comprising a soluble control analyte having a defined concentration (S sample) that is subjected to a mass spectrometric analysis leads to mass spectra comprising essentially at least the same mass peaks (at similar or even higher intensity) compared to a mass spectrum of a sample comprising said control analyte in the same defined concentration, but without a surfactant (C (control) sample), i.e. the mass spectra are essentially identical. In some embodiments, an MS-spectrum derived from an S sample may even comprise more mass peaks due to break down products of the control analyte compared to an MS-spectrum derived from a C sample, e.g., when a control analyte is digested prior to mass spectrometric analysis and break down products are hydrophobic and precipitate in a C sample prior to mass spectrometric analysis.

A suitable procedure to identify MS-compatible surfactants is for example described in WO 2006/047614. BSA, a commonly utilized test protein can be used as an exemplary intact protein and a tryptic digest of β-galactosidase (t-beta-gal) can be used as an exemplary peptide mixture. The β-galactosidase tryptic fragments have a range of solubilities from hydrophilic to hydrophobic. Moreover, many other substances can also act as control analytes as long as they are soluble enough in water so as to yield an MS-spectrum.

As a non-limiting example, a MALDI-TOF analysis of a β-galactosidase S-sample can be compared with a MALDI-TOF analysis of an equivalent C sample. The ionization suppression in the 900-3700 m/z range can be determined by comparing the matches of the mass-ions identified in the S and the C sample. The skilled person will know how to perform a useful MALDI-TOF analysis.

Preferably, the intensity of each of the aligned mass peaks of the S sample is not less than 25% compared to the intensity of the identical mass peak of the C sample, more preferably it is essentially the same or, most preferably, it is even higher than the intensity of the same peak of the C sample.

In respect of merely slightly soluble or insoluble analyte(s) or digestion products of a (control) analyte, it is preferred that the intensity of mass peaks within a mass spectrum of a sample comprising said merely slightly soluble or insoluble analyte/digestion product and an MS-compatible surfactant is at least a factor 1, 1.5, 3 5, 10, 100 or 1000 times higher than the intensity of identical mass peaks of a mass spectrum obtained for a sample containing no surfactants at all.

"Essentially identical" as used herein means that at least 60%, at least 70%, preferably at least 80%, more preferably at least 90% and most preferably about 100% of the mass peaks due to the break-down products of the control analyte of the C sample are also present in the spectra of the S sample. Search engines such as MASCOT® can be used to compare an MS-spectrum of, e.g., digested t-beta-gal or BSA with a theoretical MS-spectrum of a digest of t-beta-gal or a theoretical MS-spectrum of BSA. For the purpose of the present invention, the range from 900 to 2600 m/z should typically be considered.

In other words, a mass spectrum obtained in the presence of an MS-compatible zwitterionic or nonionic surfactant of the present invention comprises at least 60%, at least 70%, preferably at least 80%, more preferably at least 90% and most preferably 100% of the mass peaks due to the break-down products of a control analyte of a C sample.

The mass difference between a mass signal of the C sample and the identical mass signal of the S sample may vary within the error of measurement depending from the used method or apparatus. A skilled person will understand how to determine such error of measurement. For example, the mass measurement accuracy of an ion trap mass spectrometer is typically calculated between 0.5 and 2.5 dalton, whereas the mass measurement accuracy with errors less than 50 ppm or even less than 25 ppm can be achieved by measuring mass signals ranging from around 900 to 3700 dalton with MALDI-TOF applications.

Regardless of the compatibility of the surfactants of the invention, it will be understood that the concentration of a surfactant in free-flow electrophoresis and a subsequent analysis (such as MS) should be nevertheless as low as possible, preferably around its critical micelle concentration (CMC). Suitable methods in the art to determine the CMC of a surfactant are known to a person skilled in the art. Furthermore, for many surfactants, the CMC is already known.

The MS-compatible surfactants are typically used in concentrations below 100 mM. Depending on the surfactant, concentrations of below 50 mM, below 30 mM, below 15, below 5, below 1 and even below 0.1 mM may be suitable. For example, the amount of the cleavable surfactant PPS within a sample subjected to a free-flow electrophoresis as used in the present invention was 0.1% (w/v). This amount corresponds to a concentration of between 2 and 10 mM (depending on the alkyl chain combination of PPS).

A skilled person can easily identify a typical MS-compatible surfactant according to the present invention by comparing the mass spectra of a C sample and an S sample each comprising a control analyte with a distinct concentration. This method allows a skilled person to determine whether a surfactant is MS-compatible or not. Notably, it is to be expected that analytes, which are nearly insoluble or insoluble in water (without a surfactant), would hardly give an analyzable mass spectrum at all when the sample preparation does not include the use of a surfactant. Therefore, a separation of an analyte of interest by free-flow electrophoresis in the presence of an MS-compatible surfactant yields samples that are suitable for identifying and characterizing such analytes in a downstream analysis. Said downstream analysis can be mass spectrometry or any other suitable analysis method known in the art.

In a preferred embodiment, a method according to the present invention comprises performing a free-flow electrophoretic separation including at least one MS-compatible zwitterionic or nonionic surfactant according to the present invention that is comprised in a sample medium and/or within at least one separation medium. Another preferred embodiment is related to a separation medium suitable to perform a free-flow electrophoretic separation according to the present invention that comprises an MS-compatible zwitterionic or nonionic surfactant. Furthermore, yet another preferred embodiment is related to a method for separating analytes in a sample by free-flow electrophoresis, comprising performing a free-flow electrophoretic separation including at least one MS-compatible zwitterionic or nonionic surfactant, wherein said surfactant is present in the sample medium and/or in at least one separation medium. Although it is preferred that only one MS-compatible zwitterionic or nonionic surfactant is present in a sample medium or a separation medium, any combination of multiple MS-compatible zwitterionic or nonionic surfactants within a sample medium and/or a separation medium is possible. In one preferred embodiment, all zwitterionic or nonionic surfactants used in the methods of the present invention are MS-compatible surfactants. Each of the surfactants can be comprised within a sample medium and/or at least one separation medium.

Furthermore, an MS-compatible surfactant as used herein can be MS-compatible per se during the free-flow electrophoresis separation, or it can become MS-compatible through the cleavage of the surfactant. In the latter case an MS-compatible surfactant is an MS-compatible cleavable surfactant. A preferred embodiment of the present invention is a method, wherein at least one MS-compatible zwitterionic or nonionic surfactant is a cleavable surfactant, although it will be understood that optionally further MS-compatible zwitterionic or nonionic surfactants may be present. In another preferred embodiment, all MS-compatible surfactants within a sample medium and/or a separation medium are cleavable.

The terms "MS-compatible zwitterionic or nonionic cleavable surfactant", "MS-compatible cleavable surfactant" or "cleavable surfactant" are used interchangeably herein and refer to surfactants that can be cleaved into at least two moieties under particular conditions. In one embodiment, at least one of the cleaved moieties of a cleavable surfactant is MS-compatible as defined above. Such an MS-compatible moiety can be present during mass spectrometric analysis or absent, e.g., evaporated prior to MS-analysis. Non MS-compatible moieties precipitate after the cleavage or can be evaporated prior to MS analysis.

As will be explained below, it will be understood that more than two moieties may result from a cleaving step. As an example that is not to be understood as a limitation for the cleavable surfactants suitable for the methods of the present invention, an MS-compatible cleavable surfactant can be cleaved into a hydrophilic head group that is MS-compatible and remains in solution, and a hydrophobic, non-MS-compatible tail that can be easily removed from the sample by centrifugation or filtration. Accordingly, in a preferred embodiment of the present invention, at least one of the moieties of a cleaved MS-compatible zwitterionic or nonionic surfactant can be removed from a sample or from at least part of a fractionated sample by filtration, centrifugation and/or by evaporation.

Any surfactant comprising a bond that combines a hydrophobic moiety (tail) with a hydrophilic moiety (head group) that can be broken down by a cleaving agent under conditions, preferably wherein the analyte of interest is essentially stable and wherein all resulting non-MS-compatible moieties can be easily removed by centrifugation, filtration or evaporation, is suitable as an MS-compatible cleavable surfactant. In accordance with the present invention, such a bond will be referred to as a cleavable bond. Preferably, such a bond is cleaved under conditions wherein an analyte of interest is essentially stable. An essentially stable analyte under conditions suitable to cleave a cleavable surfactant is to be understood as an analyte of interest, whereof at least about 80%, about 90%, preferably about 97%, more preferably about 99% and most preferably 100% of the amount of said analyte present during a cleavage step is unmodified after the cleavage step, i.e., the analyte is mainly, preferably completely, inert to a chemical reaction under the specific conditions during the cleavage step. Inert to a chemical reaction in this context means that no covalent bond within the analyte is broken or established during the cleavage step of the surfactant.

A "cleaving agent" as used herein refers to any instrument or compound or mixture of compounds in any form suitable to selectively cleave a bond within a cleavable surfactant. Non-limiting examples for compounds suitable to selectively cleave a cleavable surfactant would be acids or bases or a solution/mixture thereof to selectively cleave a acid or base labile bond within a cleavable surfactant. This and further examples are described in more detail below. Furthermore, the term "cleaving agent" encompasses instruments suitable to selectively cleave a bond within a cleavable surfactant. Such an instrument can be, e.g., a light emitting instrument that emits light of a discrete wavelength to cleave a photo labile, cleavable surfactant.

The term "solution for cleaving a cleavable surfactant" as used herein refers to any solution comprising an agent or a composition suitable to selectively cleave one or more bonds between a linker and a moiety within a cleavable surfactant resulting in at least two moieties wherefrom moieties which are non-MS-compatible can be easily removed from the sample by centrifugation, filtration or evaporation and MS-compatible moieties may stay in solution or may likewise be removed by centrifugation, filtration or evaporation.

An MS-compatible cleavable surfactant may comprise more than one cleavable bond, e.g., two cleavable bonds resulting in three moieties from one or more cleaving steps. Each cleavable bond can be independently selected from the group consisting of a covalent bond, an ionic bond, a hydrogen bond, or a complex bond. One or more covalent bonds are preferred in the context of the present invention.

In a preferred embodiment of the present invention, at least one cleavable MS-compatible zwitterionic or nonionic surfactant in at least one fraction of a sample separated by a free-flow electrophoretic separation according to the present invention is cleaved after the electrophoretic separation, i.e., at least one MS-compatible zwitterionic or nonionic surfactant is cleavable into at least one MS-compatible moiety and a moiety that can be easily removed by filtration, evaporation or centrifugation. Again, it is noted that an MS-compatible moiety might be also removed by evaporation prior to a subsequent analysis, i.e., a non-MS-compatible moiety resulting from a cleavage step is not subjected to said downstream analysis, whereas an MS-compatible moiety might be present or, optionally, absent in a downstream analysis.

MS-compatible cleavable surfactants may comprise at least one acid labile bond, i.e., the surfactant is acid labile, or at least one base labile bond, i.e., the surfactant is base labile, or at least one photo labile bond, i.e., the surfactant is photo labile, or at least one chemo reactive bond, i.e., the surfactant is chemo reactive.

Acid and base labile cleavable surfactants may be cleaved by changing the pH of at least part of a fractionated sample/fraction, e.g., by acidifying or alkalifying of at least part of a fractionated sample/at least one fraction after an FFE separation according to the present invention comprising an acid or base labile cleavable surfactant. Photo labile cleavable surfactants may be cleaved by irradiation, i.e. the cleavage of a cleavable surfactant is carried out by subjecting at least part of a fractionated sample/at least one fraction after FFE separation comprising at least one photo labile cleavable surfactant to irradiation with light comprising or consisting of a defined wavelength suitable to selectively break the bond between a linker and a moiety of said surfactant. Chemo reactive cleavable surfactants may be cleaved by adding reactive agents, i.e. the cleavage of a cleavable surfactant is carried out by adding a reagent to at least part of a fractionated sample/at least one fraction after FFE separation that is capable of breaking a bond within a chemo reactive surfactant. For example, a suitable reactant to cleave disulfide bonds and the like is DTT (dithiothreitol) or a suitable reactant to cleave silane compounds of the general formula:

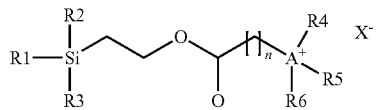

wherein R1 is selected from $C_7$-$C_{20}$ alkyl or $C_7$-$C_{30}$ alkyl aryl

R2, R3, R4, R5 and R6 are independently $C_1$-$C_5$ alkyl

A is N or P

X$^-$ is halide n is 1-5

In a preferred embodiment, a chemo reactive cleavable surfactant for use in free flow electrophoresis is {2-[(dimethyl-octyl-silanyl)-ethoxy]-2-hydroxy-ethyl}-trimethyl ammonium bromide.

Exemplary photo labile surfactants are, e.g., cinnamate esters such as 3-(2,4,6-trihydroxyphenyl)acryl acid octyl ester.

In another preferred embodiment, an acid labile, cleavable surfactant is 3-[3-(1,1-bisalkoxyethyl)pyridine-1-yl]propane-1-sulfonate (PPS).

For chemo active cleavable surfactants and especially for acid or base labile cleavable surfactants the FFE methods of the present invention provide distinct advantages over other electrophoretic methods/techniques. In fact, FFE allows using a wide variety of cleavable surfactants, which is not possible with other electrophoresis techniques. For example, acid labile cleavable surfactants such as PPS are extremely hygroscopic and are cleaved slowly by water at neutral pH, and at an accelerated rate at acidic or basic pH. According to Protein Discovery, the manufacturer of PPS, it is advised that once the package is opened to air, the contents should be immediately reconstituted in aqueous buffer (pH 7-8), protected from elevated temperatures, and used within 12 hours. This means that especially pH labile cleavable surfactants can only be used for electrophoresis if the duration of the experiment is relatively short. The maximum duration of the experiment is even lower when the pH is decreased or increased. Therefore, at non-neutral pH, the electrophoretic experiment must be carried out within an even shorter timeframe. The advantage of FFE is that an electrophoretic separation, e.g. free-flow IEF, can be performed within this short time frame required to ensure the stability of the surfactant. In contrast, IEF as performed in the first dimension of 2D-gel electrophoresis (or in the off-gel instrument) typically requires experiment times of 5 hours or more, or even longer (up to 7-9 hours or more). Thus, the cleavable surfactant would be degraded to a larger extent, especially at very low or very high pH.

Furthermore, free-flow (interval-) zone electrophoresis for separating analytes can be performed at a constant pH wherein the surfactant is stable for a sufficiently long time.

In addition, the use of counter flow media as described in the present invention can stabilize the cleavable surfactant immediately after the separation has taken place. This allows a separation of analytes at highly acidic or basic pHs in a very short time frame (e.g., down to around 5 min) followed by immediately adjusting the pH through the counter flow medium back to a pH value wherein the cleavable surfactant is essentially stable in order to increase stability of said cleavable surfactant for further processing.

Accordingly, one embodiment of the present invention relates to a FFE method, wherein a counter flow medium is used to adapt the medium conditions so as to stabilize a cleavable surfactant comprised therein after the free-flow electrophoresis, e.g., by adjusting the pH of a distinct fraction subsequent to a free-flow electrophoresis separation step.

It will be understood that these principles as described in the above non-limiting example can be extended to other types of cleavable surfactants that are stable under certain separation conditions for only a limited amount of time.

The counter flow media can also be used in a different way, e.g., to introduce a cleaving agent that cleaves the surfactant for immediate further processing of the FFE fractions.

Accordingly, another embodiment of the present invention relates to a free flow electrophoresis method wherein a counter flow medium comprising a cleaving agent comes in contact with and/or is mixed with at least part of a fraction of a sample after free-flow electrophoretic separation that comprises a cleavable surfactant in order to cleave said cleavable surfactant.

It will be understood that the use of MS-compatible surfactants is not limited to MS applications but the MS-compatible surfactants may also be present in other analytic applications subsequent to any of the free-flow electrophoresis methods of the present invention. Accordingly, the present invention also provides a method for analyzing analytes comprising a free-flow electrophoresis separation as described herein and a subsequent analysis of at least one fraction obtained from the free-flow electrophoresis that includes a technique selected from but not limited to the group consisting of free-flow electrophoresis, gel electrophoresis, 1D- and 2D-PAGE, MS, MALDI MS, ESI MS, SELDI MS, LC-MS (/MS), MALDI-TOF-MS(/MS), ELISA, IR-spectroscopy, UV-spectroscopy, HPLC, Edman sequencing, NMR spectroscopy, surface plasmon resonance, X-ray diffraction, nucleic acid sequencing, electro blotting, amino acid sequencing, flow cytometry, circular dichroism, and any combination thereof. A preferred embodiment is related to a method for analyzing analytes comprising a free-flow electrophoresis separation comprising the use of at least one MS-compatible zwitterionic or nonionic surfactant, wherein said surfactant is comprised in the sample medium and/or in at least one separation medium, and a subsequent analysis of at least one fraction obtained from the free-flow electrophoresis, wherein the subsequent analysis is selected from the group consisting of free-flow electrophoresis, gel electrophoresis, 1D- and 2D-PAGE, MS, MALDI MS, ESI MS, SELDI MS, LC-MS(/MS), MALDI-TOF-MS(/MS), ELISA, IR-spectroscopy, UV-spectroscopy, HPLC, Edman sequencing, NMR spectroscopy, surface plasmon resonance, X-ray diffraction, nucleic acid sequencing, electroblotting, amino acid sequencing, flow cytometry, circular dichroism, and any combination thereof.

In case the analyte of interest is a protein or polypeptide, a digestion step of said protein or polypeptide may be carried out prior or subsequent to the free-flow electrophoresis step. Those of skilled in the art know how to carry out a protein digestion step, e.g., using trypsin. There is also no need to remove the MS-compatible surfactants used in the free-flow electrophoresis to perform said digestion step. To the contrary, the presence of said surfactants may even improve the digestion, whereas, e.g., urea has to be at least partially removed prior to said digestion step.

In one preferred embodiment of the present invention, at least a part of a fraction or at least part of a sample is subjected to a protein digestion step. Said digestion step can be carried out prior or subsequent to the separation by a free-flow electrophoretic separation according to the present invention.

In certain embodiments, the protein digestion step is carried out in at least one fraction collected from the free-flow electrophoresis step prior or subsequent to the cleavage step of a cleavable surfactant according to the present invention.

Typically, the removal of non-MS-compatible moieties is easily achieved by methods leading to no or essentially no sample loss. A purification step according to the present invention is typically selected from the group consisting of evaporation, filtration and centrifugation to remove a precipitated moiety of a cleavable surfactant. The term "essentially no sample loss" as used herein means that less than 5% of an analyte of interest, preferably less than 1%, more preferably less than 0.2% and most preferably less than 0.1% may, e.g., stick on a filter used to remove a precipitated moiety of a cleaved surfactant or may remain within the pellet of a precipitated moiety of a cleavable surfactant that is removed by centrifugation, or may vaporize together with a moiety of a cleavable surfactant or a volatile buffer compound.

The presence of MS-compatible surfactants which are MS-compatible per se or which can be cleaved to yield at least one MS-compatible moiety and, optionally, a non-MS-compatible moiety that can be easily removed, is advantageous since purification steps that are time consuming and/or lead to sample-loss are not required. Accordingly, a preferred embodiment of the present invention relates to methods that do not require a purification step to remove surfactants selected from the group consisting of dialysis, chromatography, reversed phase chromatography, ion exchange chromatography, surfactant exchange, protein precipitation, affinity chromatography, electro blotting, liquid-liquid phase extraction, and solid-liquid phase extraction. In other words, it is not necessary to subject a fraction obtained from a FFE separation according to the present invention to such a purification step prior to a subsequent downstream analysis.

Apparatus and Elements Thereof

An apparatus suitable to perform a free flow electrophoretic separation comprises at least a separation chamber and two electrodes (an anode and a cathode). The sample to be separated is either added to the separation medium that is present in the separation space between the anode(s) and the cathode(s) of an FFE apparatus, or is preferably introduced separately into the separation space of an FFE apparatus, typically through dedicated sample inlets provided in the FFE apparatus. An apparatus suitable for FFE is shown schematically in FIG. 9. Suitable positions of a sample inlet, in the Figure referred to as S1-S4, are, e.g., situated between the electrodes and the separation media inlets (12-16) in flow direction and between the stabilization buffer inlets (11 and 17) perpendicular to the flow direction. An apparatus suitable to perform a FFE separation may further comprise counter-flow inlets (C1-C3).

The various analytes in a sample introduced into the separation medium are separated by applying an electrical field while being fluidically driven towards the outlet end of the FFE apparatus. The individual analytes exit the separation chamber through multiple collection outlets/sample outlets and are generally led through individual tubing to individual collection vessels of any suitable type. In the collection vessels, the analyte is collected together with the separation medium and, optionally, the counter flow medium. The distance between the individual collection outlets of the array of collection outlets should generally be as small as possible in order to provide for a suitable fractionation/separation. The distance between individual collection outlets, measured from the centers of the collection outlets, can be from about 0.1 mm to about 2 mm, more typically from about 0.3 mm to about 1.5 mm.

In various embodiments, the number of separation medium inlets is limited by the design of the apparatus and practically ranges, e.g., from 1 to 7, from 1 to 9, from 1 to 15, from 1 to 40 or even higher. The number of sample inlets ranges, e.g., from 1 to 36, from 1 to 11, from 1 to 5, from 1 to 4, or even from 1 to 3, whereas the number of collection outlets ranges, e.g., from 3 to 384, or from 3 to 96, although any convenient number can be chosen depending on the separation device. The number of counter flow media inlets typically ranges, e.g., from 2 to 9, or from 3 to 7. The number of provided inlets and outlets generally depends from the shape and dimensions of the separation device and separation space. Therefore, it will be appreciated that different numbers of separation medium inlets and outlets are also possible.

In FIG. 9, a separation medium flows in a laminar manner (preferably from the bottom upwards in a tilted or flat separation chamber) between and along the length of both the electrodes (large arrow). In some embodiments, the separation medium is decelerated by the counter flow (small arrow) in the vicinity of the outlets, and thus exits the separation chamber in fractions via the outlets, i.e. in some embodiments, a counter-flow medium is introduced into the separation space counter to the continuous flow direction of the bulk separation medium and sample that travels between the electrodes. Both media (separation media and counter flow media) are discharged or eluted through fractionation outlets.

A sample of, e.g., proteins to be separated is introduced into the separation medium via the sample inlet and transported by the laminar flow of the separation medium. When operated under continuous operating conditions, the protein mixture is continuously separated electrophoretically, and collected in distinct fractions according to the properties of the separation medium and the spatial separation of the analytes in the sample resulting from the electrical field generated between the electrodes in the separation medium. When operated under batch or discontinuous modes of operation, e.g., static interval mode the sample may be collected into distinct fractions with a variable chamber size that can be adjusted depending on the characteristics and needs of the electrophoresis process.

Suitable FFE devices are known in the art and are, for example, marketed under the name BD™ Free-flow Electrophoresis System (BD GmbH, Germany). In addition, suitable FFE devices that can be used with the separation and stabilizing media of the present invention have been described in a number of patent applications, including U.S. Pat. No. 5,275, 706, U.S. Pat. No. 6,328,868, pending published US applications US 2004/050697, US 2004/050698, US 2004/045826, and US 2004/026251, and International application PCT/EP2007/059010 (claiming priority from U.S. provisional applications U.S. Ser. No. 60/823,833 and U.S. Ser. No. 60/883,260), all of which are hereby incorporated by reference in their entity.

FFE Methods and Modes

Several FFE operation methods are known to those skilled in the art and are contemplated in the context of the present invention. For example, a sample can be separated according to the pI of the analytes comprised within the sample (isoelectric focusing (IEF)), the net charge density of the analytes (zone electrophoresis (ZE)) or the electrophoretic mobility of the analytes (isotachophoresis (ITP)).

Additionally, several FFE operation modes are known to those of skill in the art and are contemplated in the context of the present invention. For example, the sample and separation medium may be continuously driven towards the outlet end while applying an electrical field between the anode and the cathode of an FFE apparatus ("continuous mode"). Continuous mode in the context of FFE should be understood to mean that the injection step as well as the separation step occurs continuously and simultaneously. The electrophoretic separation occurs while the medium and the analytes pass through the electrophoresis chamber where the different species are being separated according to their pI (IEF), net charge density (ZE) or electrophoretic mobility (ITP). Continuous mode FFE allows continuous injection and recovery of the analytes without the need to carry out several independent "runs" (one run being understood as a sequence of sample injection, separation and subsequent collection and/or detection). It will be appreciated that continuous mode FFE includes separation techniques wherein the bulk flow rate is reduced (but not stopped) compared to the initial bulk flow rate while the analytes pass the separation space between the electrodes in order to increase the separation time. In the latter case, however, one can no longer speak of a true continuous mode because the reduction of the bulk flow rate will only make sense for a limited amount of a sample.

Another FFE operation mode known as the so-called "interval mode" or "static interval mode" in connection with FFE applications has also been described in the art. For example, a process of non-continuous (i.e. interval) deflection electrophoresis is shown in U.S. Pat. No. 6,328,868, the disclosure of which is hereby incorporated by reference. In this patent, the sample and separation medium are both introduced into an electrophoresis chamber, and then separated using an electrophoresis mode such as zone electrophoresis, isotachophoresis, or isoelectric focusing, and are finally expelled from the chamber through fractionation outlets. Embodiments of the '868 patent describe the separation media and sample movement to be unidirectional, traveling from the inlet end towards the outlet end of the chamber. This direction, unlike in traditional capillary electrophoresis, is shared by the orientation of the elongated electrodes. In the static interval mode described, e.g., in the '868 invention, acceleration of the sample between the electrodes caused by a pump or some other fluidic displacement element only takes place when the electrical field is off or at least when the voltage is ineffective for electrophoretic migration, i.e., when no part of the sample is being subjected to an effective electric field.

In other words, the interval process is characterized by a loading phase where the sample and media are introduced into the separation chamber of the electrophoresis apparatus, followed by a separation process where the bulk flow of the medium including the sample is halted while applying an electrical field to achieve separation. After separation/fractionation of the sample, the electrical field is turned off or reduced to be ineffective and the bulk flow is again turned on so that the fractionated sample is driven towards the outlet end and subsequently collected/detected in a suitable container, e.g., in a micro titer plate.

The so-called cyclic or cyclic interval mode in the context of FFE as used herein has been described in International application PCT/EP2007/059010 (claiming priority from U.S. provisional applications U.S. Ser. No. 60/823,833 and U.S. Ser. No. 60/883,260), hereby incorporated by reference in its entity. In sum, the cyclic interval mode is characterized by at least one, and possible multiple reversals of the bulk flow direction while the sample is being held in the electrophoretic field between the elongated electrodes. In contrast to static interval mode, the sample is constantly in motion thereby allowing higher field strength and thus better (or faster) separation. Additionally, by reversing the bulk flow of the sample between the elongated electrodes, the residence time of the analytes in the electrical field can be increased considerably, thereby offering increased separation time and/or higher separation efficiency and better resolution. The reversal of the bulk flow into either direction parallel to the elongated electrodes (termed a cycle) can be repeated for as often as needed in the specific situation, although practical reasons and the desire to obtain a separation in a short time will typically limit the number of cycles carried out in this mode.

Accordingly, in preferred embodiments, a free-flow electrophoretic separation according to the present invention is achieved by isoelectric focusing, zone electrophoresis, or isotachophoresis and the operation mode is preferably selected from continuous mode, static interval mode, or cyclic interval mode. In other words, each combination (IEF, ZE, ITP and continuous mode, static interval mode, or cyclic interval mode) is specifically contemplated herein.

Typical separation times (transit times for the analytes in the medium) during which an electrical field is applied range from a couple of minutes to about one hour per FFE separation run, although longer separations up to two hours may also be possible under certain conditions. The transit time of the analytes in the sample will be dependent on the design of the FFE chamber and the flow rate of the bulk separation medium passing through the FFE apparatus, and is usually at least 10 minutes. In general terms, separations performed in ZE mode will typically be shorter than those performed in IEF mode, particularly when operated in cyclic interval mode where the transition time can principally be extended for as long as desired, provided the conditions in the separation space remain sufficiently constant during the separation.

After having achieved the desired separation or fractionation of the analytes in the sample, the electrical field is usually turned off and the separated/fractionated analytes of interest are subsequently either collected, typically in a suitable number of fractions, from the FFE device (preparative applications), or at least detected by suitable means (analytic applications) in a suitable container, e.g., in a micro titer plate. As is readily apparent, in particular for preparative applications (which in this context is meant to include downstream analytic application such as MS where the presence of the analyte(s) is required), the MS-compatible zwitterionic or polar surfactants offer the advantage that the collected samples can be conveniently and quickly prepared for subsequent analysis.

Another aspect of the present invention also relates to the use of an MS-compatible zwitterionic or nonionic surfactant in free-flow electrophoresis. In some embodiments, the MS-compatible zwitterionic or nonionic surfactant is an MS-compatible cleavable zwitterionic or nonionic surfactant.

Yet another aspect of the present invention is related to the use of a separation medium suitable for the free-flow electrophoretic separation according to the present invention that comprises at least one MS-compatible zwitterionic or nonionic surfactant. In preferred embodiments, the separation medium is selected from but not limited to the group consisting of A/B separation media, volatile media and complementary multi pair buffer media.

Suitable Buffer Systems for Free Flow Electrophoresis (FFE)

A variety of buffer systems are useful to form a pH function profile in accordance with embodiments of the present invention. The buffer systems can be chosen from, but are not limited to, the group consisting of commercially available ampholytes (for example sold under the name Servalyt® by Serva Electrophoresis GmbH, Germany), complementary multi-pair buffer systems (e.g., BD FFE Separation mediums 1 and 2 sold by BD GmbH, Germany), volatile buffer systems, and binary buffer systems referred to as A/B media.

In preferred embodiments of the present invention, the buffer system of a separation medium comprising at least one MS-compatible zwitterionic or nonionic surfactant is selected from the group consisting of A/B media, volatile media and complementary multi pair media as described in more detail below.

Especially methods comprising volatile separation media as described in U.S. Pending Provisional Ser. No. 60/945,246 and MS-compatible surfactants offer the advantage that a sample separated by a free-flow electrophoresis step can be directly used for a subsequent analysis such as MS without the need of any purification step except, an optional easy removal of non-MS-compatible moieties of cleaved MS-compatible surfactants and/or evaporation of buffer compounds.

Therefore, a preferred embodiment of the present invention is a method comprising a volatile buffer system and MS-compatible zwitterionic or nonionic polar surfactants. Fractions comprising said combination can be easily further concentrated, by removing the volatile buffer compounds through simple means such as evaporation, or can be directly prepared for subsequent use in, e.g., an MS analysis without further purification steps, except, if necessary, removal of non-MS-compatible moieties of cleaved MS-compatible surfactants.

As used herein, the term "buffer systems" refers to a mixture of mono, di- or tri-protic/basic compounds, which are able to maintain a solution at an essentially constant pH value upon addition of small amounts of acid or base, or upon dilution.

A "buffer compound" as used herein means a compound which forms alone or together with a second or further compound(s) a buffer system.

Each medium component preferably comprises anions and cations with electrophoretic mobilities less than or equal to about $40 \times 10^{-9}$ m$^2$/V/sec, and more preferably even less than 30, 25 or even $20 \times 10^{-9}$ m$^2$/V/sec.

The term "separation media" as used herein refers to buffer media which are suitable to form a separation zone within an apparatus suitable to perform a free-flow electrophoresis method. Several useful separation media are described herein.

A "separation zone" as used herein should be understood to be located between the two electrodes of an apparatus suitable to perform a free-flow electrophoretic separation. A separation zone is formed by at least one separation medium. A typical separation zone may be encompassed on each side by a stabilizing medium, a focus medium or an electrode medium.

The term "counter flow medium" as used herein is typically an aqueous medium such as a separation medium or a part thereof (e.g., simply water), but may further comprise additives such as surfactants. Furthermore, such additives may be substances to cleave a surfactant according to the present invention, e.g., such as bases or acids, fluorine or fluoride containing compounds or any other compound capable of cleaving a cleavable surfactant. In another embodiment, a counter flow medium can have a different pH compared to a separation medium. A different pH can for example be achieved by changing the concentration of at least one buffer compound within the counter flow media compared to the concentration of said buffer compound(s) also used within the separation medium. Furthermore, the pH can be changed by adding strong acids or bases. In a preferred embodiment, the buffer system used for a counter flow medium is selected from the group consisting of A/B media, volatile media and complementary multi pair media. The different pH may cause the cleavage of a cleavable surfactant, or may change the pH of a separation medium to a pH wherein an acid or base labile surfactant is less labile, i.e. essentially not cleaved or cleaved slower compared to the pH of the separation medium.

So-called "stabilizing media" serve to stabilize the electrochemical conditions in the separation chamber by preventing undesirable effects or artifacts which may otherwise be observed during the electrophoretic separation process, particularly in free-flow electrophoresis. The stabilizing media are generally located in the vicinity of the electrodes, i.e., between the anode/cathode and the separation zone, respectively. The stabilizing media disclosed herein should generally have a higher electrical conductivity than the separation medium used in concert with the stabilizing media. The higher conductivity prevents a cross-contamination between the separation area and the electrode compartment of the electrophoresis device and also serves to avoid the unwanted accumulation of separated particles or analytes at the electrodes. Moreover, all compounds such as ions, additives and the like which are required within the separation medium can be supplied or replenished from the stabilizing media present in the vicinity of the cathode and anode, respectively.

A stabilizing medium is generally characterized by having an electrical conductivity that is higher compared to the conductivity in the separation medium adjacent to said stabilizing medium. The conductivity may be increased by a factor of 2, preferably a factor of 3 and most preferably a factor greater than 3. The differences in conductivity between the separation media and the stabilizing media is achieved by a variety of ways, for example by adding further electrically conductive ions to the stabilizing media or by increasing the concentration of the buffer compounds in the stabilizing media compared to the concentration of said buffer compounds in the separation medium as described in further detail herein above, or by adding a strong acid or a strong base. For example, an increased conductivity of a cathodic stabilizing medium may be achieved by adding a strong base, or an increased conductivity of an anodic stabilizing medium may be achieved by adding a strong acid. Such strong acids or bases may be selected from but not limited to NAOH, KOH, $H_2SO_4$ or $H_3PO_4$.

Although the electrical conductivity of the stabilizing media will be higher than the conductivity of the adjacent separation medium, the pH of the stabilizing media may be greater, nearly equal or even lower than the pH of the adjoining separation medium, depending on the circumstances of the separation problem. For example, an anodic stabilizing medium has a pH that is equal or lower than the pH of the separation medium adjacent to said anodic stabilizing medium, or a cathodic stabilizing medium has a pH that is equal or higher than the pH of the separation medium adjacent to said cathodic stabilizing medium The buffer compounds of the stabilizing media can be identical with the buffer compounds of the separation media or can be different.

In certain embodiments of the present invention, the separation of at least one analyte may be conducted in parallel mode, i.e. two samples can be separated at the same time within a separation chamber of an apparatus suitable to perform a free-flow electrophoresis. For the latter, it is required to physically separate the separation zones within an apparatus suitable to carry out a free-flow electrophoresis by virtue of an inter-electrode stabilizing medium. The term "inter-electrode stabilizing medium" as employed herein refers to a medium composed of two mandatory components: One cathodic inter-electrode stabilizing medium and one anodic inter-electrode stabilizing medium. It is readily apparent that the use of the terms anodic and cathodic refers to the relative position of the correspondingly named inter-electrode stabilizing medium between a separation zone and the anode and cathode, respectively. For example, a typical order (from anode to cathode of the FFE apparatus) will be a stabilizing medium, a separation zone and then a cathodic inter-electrode stabilizing medium followed by an anodic inter-electrode stabilizing medium, a second separation zone and finally a (cathodic) stabilizing medium. In the exemplary set-up described above, the cathodic inter-electrode stabilizing medium is thus closer to the physical anode of the FFE apparatus than the anodic inter-electrode stabilizing medium. Such a parallel mode, e.g., is disclosed in International application PCT/EP2007/056167 (claiming priority from U.S. provisional applications U.S. Ser. No. 60/805,248 and U.S. Ser. No. 60/821,491).

When practicing the above embodiments of the present invention, the inter-electrode stabilization zone may conveniently be established by introducing the two components of the inter-electrode stabilizing medium into the FFE apparatus in between the plurality of separation zones.

Typically, the inter-electrode stabilizing medium will have a conductivity higher than that of the first and second separation zone adjacent to said inter-electrode stabilizing medium, thereby preventing the crossover of ionic species between the separation zones as well as crossover of anionic and cationic species of the anodic and cathodic inter-electrode stabilizing medium into the adjacent separation zones.

The term "focus medium" as used herein refers to a medium comprising an acid for an anodic focus medium or a base for a cathodic focus medium which form a conductivity step regarding the adjacent pH function, pH gradient or pH separation plateau, forming a focus zone wherein the movement of analytes towards the anode or cathode is essentially reduced to zero due to a conductivity step. The concentration of the acid and base will be chosen so as to be sufficient to increase the conductivity of said focus medium, preferably by a factor of at least 2, and more preferably of at least 3, at least 5, or even more with regard to an adjacent pH separation plateau, pH gradient or pH function. This abrupt increase in the electrical conductivity of the medium is useful to accumulate analytes with a different pI than the pI of an analyte to be separated on a pH separation plateau at the border of the two media having different conductivity values since the mobility of analytes moving to the anode or cathode, respectively is reduced to essentially zero.

Complementary Multi-Pair Buffer Systems

In certain embodiments of the invention, a buffer mixture used to generate the pH gradient may be comprised of carefully matched acids and bases such that the mixture may provide a smooth pH gradient when current flows through the buffer system. A mixture of low molecular weight organic acids and bases are chosen that enable an increased buffering capacity compared to commercially available high molecular weight ampholytes. These mixtures of carefully matched acids and bases are extremely well characterized in terms of molecular weight, pI, purity, and toxicity. Generally, the acids and bases have a smaller molecular weight than those of commercial ampholytes. Suitable complementary multi-pair buffer systems are known in the art. Specifically, a mixture with a pH range from 3 to 5 is sold as BD FFE Separation medium 1 while a mixture with a pH range from 5 to 8 is sold as BD FFE Separation medium 2 by BD GmbH Germany. These buffer systems have, for example, been described in general form in US patent application US 2004/0101973 and in EP-A-1 320 747 which are incorporated herein by reference in their entirety. Complementary multi-pair buffer systems as described above are referred herein as "CMPBS" or "CMPBS media".

Volatile Buffer Systems

In other embodiments of the present invention, volatile buffer systems can be used to perform a free-flow electrophoretic separation of a sample. These buffer systems are disclosed in U.S. Pending Provisional Ser. No. 60/945,246 and offer the particular advantage that they can be removed residue-free from the recovered fractionated sample after an FFE separation step or are MS-compatible per se and can remain in the sample.

A volatile separation medium according to embodiments of the present invention should be understood to represent, in its ready-to-use form, a composition, preferably an aqueous composition, that includes a buffer system comprising at least one buffer acid and at least one buffer base, wherein all of the buffer compounds are volatile. Optionally, at least one of the buffer compounds may be capable of functioning as a (volatile) matrix for mass spectrometry, particularly in MALDI applications.

The term "volatile" used in connection with the buffer compounds herein should be understood to refer to the buffer compound's ability to be completely removable from an aqueous sample under suitable conditions, i.e., the buffer compound can be evaporated without leaving behind any residual compound (e.g., a salt), i.e. residue-free. In its broadest meaning, a volatile buffer compound according to embodiments of the present invention can be removed residue-free under conditions selected from, but not limited to, the group of reduced atmospheric pressure, increased temperature, supply of energy by irradiation (e.g. UV light, or by applying a laser light), or any combination thereof, although it will be appreciated that a volatile buffer compound must essentially be non-volatile under FFE working conditions (i.e., atmospheric pressure and temperature ranges of typically between 0 and 40° C. as explained hereinabove).

In this context, the skilled person will understand that, in one embodiment of the invention, the analyte(s) that is (are) present in a sample comprising volatile buffer compounds will be non-volatile under the afore-mentioned conditions, i.e., the analyte(s) is (are) essentially not modified (e.g., by fragmentation or oxidation) and remain(s) in solution or in its (their) solid state. In certain embodiments, particularly under mass spectrometric working conditions, the analyte(s) will also be volatile and will be ionizable (required for detection by MS).

The term "non-volatile under FFE working conditions" as used herein means a volatility of a buffer compound leading to a concentration reduction of the respective buffer compound in the separation medium of less than 5% w/v or, preferably less than 2% w/v under working conditions and during the separation period of FFE. Most preferably, no concentration reduction will be observed at all under working conditions and the separation period of FFE.

The term "residue-free" in the sense of the present invention is to be understood that the volatile compound itself evaporates completely, but that residues caused, e.g., by an impurity of the used substances, may be non-volatile. However, it is well known to those of skill in the art that only compounds having the highest purity grade available should be used for analytic purposes, and particularly so for mass spectrometric analysis.

Removal of the solvent and buffer compounds by "evaporation" as used herein should be understood to refer to a removal from the analytes of interest through transferring the compounds into the gas phase and subsequent elimination of the gas phase by suitable means. Thus, evaporation as defined herein is different from eliminating the buffer compounds by techniques commonly referred to as buffer exchange (sometimes also referred to as "desalting"), including column chromatography, dialysis or cut-off filtration methods, or techniques known as solid phase extraction or analyte precipitation. Alternatively, in certain applications that are not included under the term evaporation, the buffer compounds present in salt form are simply washed away with water, although this obviously leads to an undesirable loss of sample material and, moreover, non-quantitative removal of the buffer compounds. Those of skill in the art will appreciate that the volatile buffer compounds as defined herein could, at least in principle, likewise be removed by such buffer exchange or solid phase extraction techniques, although this would of course neglect the distinct advantage offered by the volatility of the buffers (and makes no sense in view of the potential problems connected with buffer exchange techniques, e.g., difficult handling and low sample recovery).

Suitable exemplary techniques for removing the solvent and the volatile buffer compounds from a sample collected from an FFE separation step by evaporation include, but are not limited to, vacuum centrifugation using suitable devices such as a centrifugal evaporator or a vacuum centrifuge known for example under the name SpeedVac®, by lyophilization or by a (gentle) heating of the aqueous sample. Other possibilities to evaporate the solvent and the buffer compounds include evaporation by subjecting the sample to reduced pressure conditions, e.g., applying a vacuum to the sample placed on a target plate used in mass spectrometric analysis. Those of skill in the art will appreciate that most mass spectrometric methods operate under vacuum conditions (for example vacuum MALDI) so that the volatile buffer compounds are conveniently removed after the introduction of the sample into the MS instrument, but prior to ionization.

Preferably, the volatile buffer compounds are removable under conditions of reduced pressure and/or increased temperature. Moreover, in other embodiments, the volatile buffer compounds may even be evaporated under ambient temperature and atmospheric pressure conditions, particularly if the volatile buffer-containing sample is present in a small volume (e.g., for mass spectrometric analysis). However, in most cases at least some buffer solution will not evaporate readily under those conditions. In yet other embodiments, the volatile buffer compounds can only be removed under harsher conditions (e.g., in vacuum and/or high temperatures, optionally with irradiation, such as under mass spectrometric working conditions).

In certain embodiments of the present invention, the FFE separation media comprise volatile buffer compounds wherein at least one of the volatile buffer compounds may act as a (volatile) matrix for mass spectrometric analysis, i.e., the compound can only be removed under mass spectrometric working conditions. It will be understood that the term matrix in the context of mass spectroscopy (MS) as used herein is different from the term "matrix" used in the context of electrophoresis (e.g., polyacrylamide or agarose). Therefore, in some embodiments wherein the downstream analysis is for example a MALDI application, a matrix component for MALDI analysis is added to the analyte buffer solution prior to mass spectrometric analysis.

Examples for volatile buffer systems include, but are not limited to combinations of TRIS/acetic acid, diethanolamine/picolinic acid, dimethylamino-proprionitril/acetic acid, 2-pyridine ethanol/picolinic acid, benzylamine/2-hydroxypyridine, tri-n-propylamine/trifluoroethanol, and the like.

Binary Buffer Systems (A/B Media)

Binary buffer systems as defined below are referred to herein as "A/B media" and are disclosed in detail in co-pending U.S. provisional application U.S. Ser. No. 60/885,792. The separation medium comprises at least one buffer acid and at least one buffer base, with the proviso that the pKa value of the buffer acid must be higher than the pH of the separation medium and the pKa of the buffer base is lower than the pH of the separation medium. Put another way, the pKa of the buffer acid will be higher than the pKa of the buffer base.

The pH profile exhibited by the separation medium may be essentially linear (i.e., without any major pH steps during electrophoretic separation). Depending on the stabilizing media employed as well as the pKa differences between the buffer acid and the buffer base, the A/B separation media according to this aspect of the invention will offer an essentially constant (i.e., flat) pH profile, or a rather gentle/flat pH gradient within the separation chamber. It will be appreciated that said separation media providing a zone with an essentially constant pH in the separation chamber between the electrodes are particularly useful for the creation of pH separation plateaus in accordance with the methods described herein. However, since the A/B media may also form flat- or ultra flat pH gradients, they can also be used for the creation of pH functions or pH gradients as defined herein.

Preferably, the A/B media employing at least one buffer acid and one buffer base in the above aspect of the present invention are characterized by a pKa difference between the at least one buffer acid and the at least one buffer base of between about 0.5 and 4 pH units, wherein the pKa of the acid must be higher than the pKa of the base as explained above. In preferred embodiments, the ΔpKa is between 1.2 and 1.8, which is particularly useful for pH separation plateaus having a constant pH within the separation chamber of an FFE apparatus. In other preferred embodiments, the ΔpKa will be between about 2.5 and 3.3, the latter being particularly suitable for flat pH-gradients.

One characteristic of the A/B media is that the electrical conductivity of the medium is relatively low, although it will be appreciated that the conductivity must be sufficiently high to achieve acceptable separation of the analytes in a reasonable amount of time. Thus, the conductivity of the A/B media is typically between 50 and 1000 μS/cm, and more preferably between 50 and 500 μS/cm, although those of skill in the art will be aware that the exact conductivity in the separation medium will of course depend on the specifics of the separation/fractionation problem, the presence of other charged species in the medium (e.g., ions required for sample/analyte stability) and the electrochemical properties of the analyte.

Preferably, the A/B media comprise only one buffer acid and one buffer base. In other words, such separation media represent binary media wherein one acid function of a compound and one base function of the same or another compound essentially serve to establish a separation medium with the desired pH and conductivity profile. While good results may also be achieved with two or more buffer acids and buffer bases in the separation medium, it is typically advantageous to use as few components as possible, not only because it is easier to prepare and possibly cheaper to use, but also because the electrochemical properties of the medium will become more complex if the number of charged species present in the separation chamber is increased.

The concept of A/B media is described in detail in co-pending U.S. provisional application U.S. Ser. No. 60/885, 792, which is incorporated herein by reference in its entirety. Suitable buffer bases in this context are, for example, taurine, glycine, 2-amino-butyric acid, glycylglycine, β-alanine, GABA, EACA, creatinine, pyridine-ethanol, pyridine-propanol, histidine, BISTRIS, morpholinoethanol, triethanolamine, TRIS, ammediol, benzylamine, diethylaminoethanol, trialkylamines, and the like. Suitable buffer acids are, for example, HIBA, acetic acid, picolinic acid, PES, MES, ACES, MOPS, HEPES, EPPS, TAPS, AMPSO, CAPSO, α-alanine, GABA, EACA, 4-hydroxypyridine, 2-hydroxypyridine, and the like, provided the pKa relationships between the buffer acid and buffer base as described above is met.

Furthermore, in the methods of the present invention binary buffer systems as disclosed in, e.g., U.S. Pat. No. 5,447,612 for separating analytes by FFE can also be employed. These binary media may be suitable for forming relatively flat pH gradients of between 0.4 to 1.25 pH units.

Additives

The separation media suitable for the methods of the present invention may further comprise one or more additives. Additives in accordance with embodiments of the present invention are compounds or ions that do not (or at least not significantly) contribute to the buffering capacity provided by the buffer acids and the buffer bases. Generally, the number and concentration of additives should be kept to a minimum, although it will be appreciated that certain analytes or separation problems require the presence of additional compounds either for maintaining analyte integrity or for achieving the desired properties of the medium (e.g., viscosity adaptation between various separation media, etc.).

Possible additives are preferably selected from other acids and/or bases, so-called "essential" mono- and divalent anions and cations, viscosity enhancers, affinity ligands, and the like.

Essential mono- and divalent anions and cations in the sense of the present application are ions that may be needed for maintaining the structural and/or functional integrity of the analytes in the sample. Examples for such essential anions and cations include, but are not limited to magnesium ions, calcium ions, zinc ions, Fe(II) ions, chloride ions, sulfate ions, phosphate ions or complexing agents such as EDTA or EGTA, or azide ions (e.g., for avoiding bacterial contamination), and the like.

Examples for possible acids and bases include small amounts of strong acids or bases (e.g., NaOH, HCl, etc.) that are completely dissociated in solution, or very weak acids or bases that are present as essentially non-dissociated species in the medium (i.e. having a pKa that is more than about 4 units away from the pH of the medium).

Viscosity enhancers commonly used in the separation media may include polyalcohols such as glycerol or the various PEGs, hydrophilic polymers such as HPMC and the like, carbohydrates such as sucrose, hyaluronic acid, and the like. Viscosity enhancers may be required to adapt the viscosity of the separation medium to the viscosity of the sample introduced into the separation space, or to the viscosity of other separation and/or stabilizing media within the separation chamber in order to avoid turbulences created by the density or viscosity differences between sample and medium or between different adjacent media.

Additional additives that may be present include chiral selectors such as certain dextrins including cyclodextrins, or affinity ligands such as lectins and the like.

In certain cases, it may be required to add reducing agents to prevent the oxidation of an analyte in the solution. Suitable reducing agents that may be added to the sample and/or the separation medium includes mercaptoethanol, mercaptopropanol, dithiothreitol (DTT), ascorbic acid, sodium or potassium metabisulfite, and the like.

In any event, because many of the aforementioned additives are electrically charged, their concentration should be kept as high as needed but at the same time as low as possible so as to maintain the electrical conductivity of the separation medium within the desired (low) range.

It should be noted that additives which are not volatile under any condition as described under the volatile buffer section or potentially interfere with the subsequent analysis, e.g., MS analysis, should at any rate be avoided.

Kits

It will be apparent to those skilled in the art that the surfactants used in the methods contemplated herein may be used as part of a sample medium and/or as part of at least one separation medium.

Accordingly, one aspect of the present invention also relates to a kit for carrying out a FFE separation (such as IEF, ZE and ITP) of analytes in a sample according to embodiments of the present invention, wherein the kit comprises at least one MS-compatible zwitterionic or nonionic surfactant. In one embodiment, at least one MS-compatible zwitterionic or nonionic surfactant is a cleavable surfactant.

It will be understood that the surfactant or the surfactants is/are delivered as part of a medium or separately in one or a plurality of containers.

In addition to at least one MS-compatible zwitterionic or nonionic surfactant, a kit can further comprise a separation medium or a plurality of separation media. The medium or the media can be delivered in one or can be separately delivered in a plurality of containers. If more then one container is provided, at least two containers can contain the same medium or all batches can individually contain different media. The number of separation media can be between 1 and 15, or between 3 and 12, or between 4 and 9.

In a preferred embodiment of the present invention, a separation medium in the kit is selected from but not limited to the group consisting of A/B buffer media, volatile buffer media and complementary buffer pairs media. A kit may comprise several different media combinations, e.g. a volatile buffer medium and a multi pair buffer medium. Furthermore, a separation medium additionally comprises additives such as surfactants, viscosity enhancers, "essential" anions and cations, and the like.

In case a kit comprises a separation medium comprising an A/B medium, it is preferred in one embodiment that the A/B medium is capable of forming a separation zone wherein the difference between the minimum pH and the maximum pH within the separation chamber of an FFE apparatus during electrophoresis is less than about 0.2, and preferably less than 0.1 pH units. Furthermore, it is preferred that the pH should be essentially constant during electrophoresis. A kit comprising such A/B media are especially adjuvant to perform in free-flow zone electrophoresis, i.e. such a kit would be for use in free-flow zone electrophoresis.

In another embodiment of the present invention, it is preferred that the A/B medium is capable of forming a separation zone wherein the pH forms an essentially linear gradient between the electrodes within the separation chamber during electrophoresis, and in yet another embodiment it is preferable that the A/B media are capable of forming a separation zone wherein the pH is essentially non-linear within the separation chamber during electrophoresis. Such kits would be suitable for use in free-flow isoelectric focusing.

In case a kit comprises a separation medium containing a volatile buffer medium, it is preferred that at least one buffer compound is volatile under reduced pressure, is volatile at increased temperature, is volatile when subjected to irradiation, or is volatile under mass spectroscopy working conditions.

In addition to one or more separation media and at least one surfactant according to the present invention, a kit for carrying out a FFE method in accordance with embodiments of the present invention may further comprise at least one stabilizing medium as defined hereinabove. The stabilizing medium may be a cathodic stabilizing medium and/or an anodic stabilizing medium. They are generally located between the anode/cathode and a separation medium, respectively.

Since anodic and cathodic stabilization are both particularly useful for successful electrophoretic applications, particularly in FFE, the kit will, in addition to the separation media, preferably comprise one anodic and one cathodic stabilizing medium as defined herein.

In some embodiments of the present invention, a stabilizing medium is located between two pH function profiles, enabling a parallel separation of two different samples at the same time within a FFE apparatus containing two electrodes.

In further embodiments, a kit may further comprise at least one focus medium as defined above.

In yet other embodiments, a kit may further comprise an agent useful to selectively cleave one or at least one cleavable MS compatible zwitterionic or non-ionic surfactant. Such an agent can be a solid compound or a mixture of solid compounds or a solution to, e.g., change the pH within a solution comprising a sample or a part of a sample or a solution containing a compound suitable to cleave a cleavable surfactant according to the present invention.

It is to be understood that in certain embodiments according to the present invention the kit will preferably include all media or compounds required for a given electrophoretic separation, e.g., an anodic and a cathodic stabilizing medium, as well as a separation medium (which consists of several sub-fractions as explained above) and/or an agent to cleave a cleavable surfactant. In such embodiments, the separation media and stabilizing media will of course be selected so as to be useful for the intended protocol.

The kit may comprise the various media as one or more aqueous solutions that are ready to be used in a free-flow electrophoresis according to the present invention (i.e., all components are present in the desired concentration for the electrophoretic separation problem), or it may contain one or several of the media in the form of a concentrated solution that is to be diluted with a pre-determined amount of solvent prior to their use. Preferably, such a stock solution has a 1.5×, 2×, 2.5×, 3×, 4×, 5×, 6×, 10×, 20×, 25×, 50×, 75×, 100×, 150×, 200× and 1000× higher concentration as for use in a free-flow electrophoresis according to the present invention.

Alternatively, the kit may comprise one or several media and/or components in dry form or lyophilized form that are to be dissolved with solvent, preferably water, to the appropriate concentration for use in a free-flow electrophoretic methods according to the present invention.

A kit according to the present invention comprises the various ingredients of a medium in several, but preferably in one container, which is then reconstituted with a predetermined amount of solvent prior to its use in an electrophoretic separation process.

It will be understood that all of the preferred separation media described herein, as well as the preferred cathodic and/or anodic stabilizing media and focus media may be included in the kits of the present invention.

It is generally preferred that each medium (separation medium, cathodic stabilizing medium, anodic stabilizing medium, counter flow medium etc.) will be present in a separate container, i.e. each component, each dried component and/or each stock solution of said kit is separately placed in a sealed container although it will be apparent to those of skill in the art that other combinations and packaging options may be possible and useful in certain situations. For example the separation media for IEF applications may consist of a distinct number of "sub-fractions" having different concentrations of the ingredients (and thereby a different pH) in order to create a pre-formed pH gradient within the electrophoresis apparatus. In one embodiment, the pH of each separation medium used to form the gradient is different. The number of sub-fractions employed in IEF applications will depend on the separation problem, the desired pH span achieved with the separation medium and the electrophoresis apparatus used for the separation. In FFE applications, the apparatus will typically comprise several media inlets (e.g., N=7, 8 or 9 inlets), so that the sub-media creating the separation space within the apparatus may be introduced into at least one to a maximum of N-2 inlets (at least one inlet on each side is usually reserved for a stabilizing medium, if present). The number of separation media which are inserted into an apparatus suitable for FFE is thus typically between 2 and 15, or between 3 and 12, or between 4 and 9.

In particularly preferred embodiments, the separation media in the kit will be formed by binary buffer systems, comprising only one buffer acid and one buffer base. It is contemplated that all of the separation media described herein, be they preferred or not, may be included in the kits of the present invention.

Further to suitable media and/or other compounds in various numbers and delivery form, a kit may comprise a product manual that describes one or more experimental protocols, and optionally storage conditions for the components.

Generally, the kits according to the present invention are useful in free-flow electrophoretic separation protocols as described herein.

It will be apparent to those of skill in the art that many modifications and variations of the embodiments described herein are possible without departing from the spirit and scope of the present invention. The present invention and its advantages are further illustrated in the following, non-limiting examples.

Example 1

Separation of Serum from Python Sebae with and without PPS

Serum was taken from python sebae. The serum sample was diluted 1:10 in the separation medium. The separation medium contained only buffer components that are well known to be compatible with MALDI-TOF. In addition, one experiment was performed using PPS, a MALDI-TOF compatible cleavable surfactant, to the sample as well as the separation medium.

The separation of the sample was carried out on a BD™ Free-flow Electrophoresis System in free-flow isoelectric focusing (FF-IEF) mode. The apparatus was set up comprising nine media inlets (E1-E9) and four sample inlets (S1-S4). Anodic stabilizing medium was introduced into inlet E1. The cathodic stabilizing medium was introduced into inlet E9 and the sample was introduced via sample inlet S2. The voltage applied was 550V and the current was 105 mA. The sample and the media were introduced at a flow rate of 2 ml/h and 150 ml/h, respectively.

Separation and stabilizing media within the FFE apparatus:

ible or can be removed by evaporation prior to an MS-analysis.

96 fractions were collected in each of the two experiments. 0.2 mL were taken of each fraction for an SDS-PAGE. The SDS-PAGE gel images (silver stained) of every second fraction of the separated samples (one sample with, one sample without PPS) are shown in FIG. 1.

Although the separation pattern look quite similar, some precipitation was observed in the separation chamber without surfactant in the separation medium. This was significantly less pronounced using 0.1% PPS in the separation medium.

Figure 2:
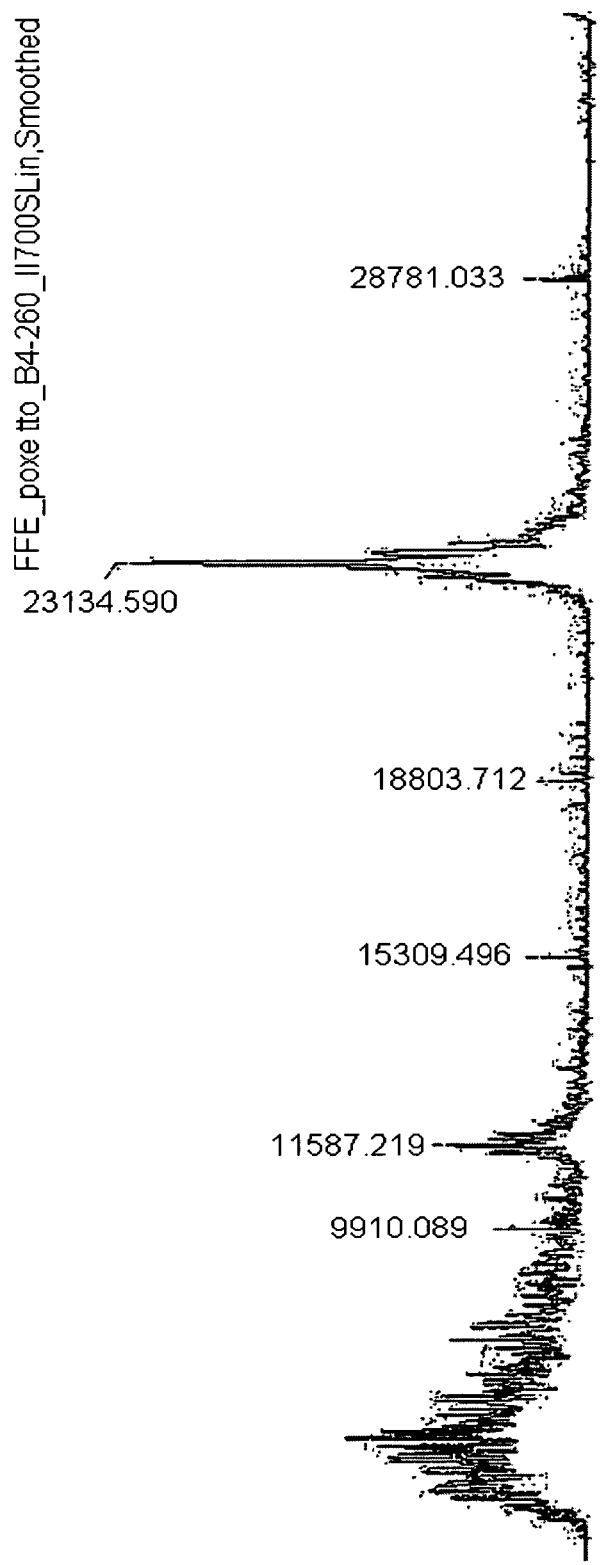
FIG. 2: A MALDI TOF mass spectrum of fraction 26 of the PPS containing sample.

The separation media were completely free of glycerol and other components that are known to interfere with the MALDI-TOF measurements. The fraction can therefore be applied directly onto the MALDI target. A mass spectrum of the 25 kDa protein of fraction 26 is shown in FIG. 2.

Example 2

Separation of Peptides Generated from HELA Cells with and without PPS

To confirm the suitability of zwitterionic surfactants such as PPS for FFE, the separation profile of samples (and FFE methods) containing PPS were compared with the separation profile of samples (and FFE methods) without PPS. In one example, two samples of $10^8$ HeLa cells each were sonicated in HBS buffer (10 mM HEPES pH 7.9, 1.5 mM $MgCl_2$, 10 mM KCl+protease inhibitors complete mini tablet (1 tablet for 10 ml; Roche #11836153001)). Soluble proteins were separated from insoluble cell fragments such as membranes and membrane proteins by ultracentrifugation.

100 mM ammonium bicarbonate buffer were added to the supernatant (soluble proteins 3 mg/ml) and TCEP (Tris(2-carboxyethyl)phosphine hydrochloride) to a final concentration of 5 mM was added (incubation for 60 min), then IAA (iodoacetamide) was added to a final concentration of 15 mM (incubation 60 min). Trypsin (modified, sequencing grade, Promega) was added to a final ratio of 1:37.5 enzyme:protein and incubate of for a minimum of 4 hours at 37° C. The digestion was stopped by acidifying the solution with 0.1% TFA (trifluoroacetic acid).

The peptides were purified using SepPak® Vac 1 cct C18 cartridges (Waters). The procedure includes washing the cartridge

|  | Media inlet | | | | | | |
|---|---|---|---|---|---|---|---|
|  | E2 | E3 | E4 | E5 | E6 | E7 | E8 |
| Media | 150 mM HAc/ 25 mM Tris/ 100 mM betaine | 300 ml 10 mM Tris/300 µl HAc | | | 200 ml 10 mM HAc/260 mg Tris | | 100 ml 150 mM HAc/150 mM Tris/560 mg Tris |
| pH | 3.95 | 4.85 | | | 7.08 | | 7.78 |
| Conductivity/ [µS/cm] | 1475 | 622 | | | 611 | | 6800 |

Anodic stabilizing medium: 1567 mM HAc/450 mM Tris (pH=4.11; conductivity: 6610 µS/cm) (E1)

Cathodic stabilizing medium: 450 mM HAc, 900 mM TRIS (pH=8.23; conductivity: 6220 µS/cm) (E9)

Counter flow medium: Water (CF1-CF3)

The above described separation media are volatile separation media, i.e. the buffer compounds are either MS-compattridge with acetonitrile and 0.1% TFA, loading the sample, washing the sample with 0.1% TFA, eluting peptides with acetonitrile and evaporating to dryness by vacuum centrifugation. The first sample was reconstituted in 1 ml separation medium for the 3-8 gradient, the second sample was reconstituted with 1 ml separation medium for the 3-8 gradient and 0.1% PPS.

The 3-8 gradient used herein is a complementary multi-pair buffer system as described above.

The isoelectric focusing electrophoresis was carried out on a BD™ Free-flow Electrophoresis System in FF-IEF mode. The apparatus was set up comprising seven media inlets (E1-E7) and four sample inlets (S1-S4). Anodic stabilizing medium was introduced into inlets E1 and E2. The cathodic stabilizing medium was introduced into inlets E5 to E7 and the sample was introduced via sample inlet S2. The voltage applied was 400 V and the current was 29 mA. The sample and the media were introduced at a flow rate of 2 ml/h and 50 ml/h, respectively.

Separation and Stabilizing Media within the FFE Apparatus:

Separation media (E3-E4): 250 mM mannitol, 35 g/200 ml Pro 3-8

Pro 3-8 is typically a composition of:

| pH 3-8 | Stock sol (mM) | MW | 250 ml Stock sol. (mg) |
|---|---|---|---|
| HIBA | 30 | 104.11 | 780.825 |
| Iso butyric acid IBA | 35 | 88.11 | 770.9625 |
| 2-4-(Pyridyl)ethansulfonic acid PES | 40 | 187.21 | 1872.1 |
| MES | 45 | 195.20 | 2196 |
| ACES | 20 | 182.2 | 911 |
| MOPSO | 50 | 225.27 | 2815.875 |
| MOPS | 50 | 209.27 | 2615.875 |
| HEPES | 50 | 238.31 | 2978.875 |
| EPPS | 80 | 252.33 | 5046.6 |
| TAPS | 100 | 243.28 | 6082 |
| Betaine Anhydrous | 100 | 117.15 | 2928.75 |
| 2-A-butyric acid | 80 | 103.10 | 2062 |
| Nicotinamid | 60 | 122.13 | 1831.95 |
| Glycyl-glycin | 60 | 132.12 | 1981.8 |
| Piperidin-4-carbonic acid | 50 | 129.16 | 1614.5 |
| GABA | 40 | 103.12 | 1031.2 |
| EACA (6-Amino-caproic acid) | 30 | 131.18 | 983.85 |
| 3-(Hydroxymethyl)pyridine (4° C.) | 40 | 109.13 | 1091.3 |
| 2-(2-Hydroxyethyl)pyridine | 40 | 123.16 | 1231.6 |
| 4-Pyridinpropanol | 35 | 137.18 | 1200.325 |
| BISTRIS | 30 | 209.24 | 1569.3 |
| Gluconic acid | 25 | 196.16 | 1226 |
| N-Acetylglycine | 20 | 117.10 | 585.5 |

Anodic stabilizing medium: 100 mM $H_2SO_4$, 30 mM acetylglycine, 200 mM taurine, 50 mM betaine (pH=1.2; conductivity: 24600 µS/cm) (E1 and E2);

Cathodic stabilizing medium: 150 mM NaOH, 75 mM ethanolamine, 150 mM AMPSO ((N-(1,1-Dimethyl-2-hydroxyethyl)-3-amino-2-hydroxypropansulfonic acid), 75 mM TAPS ((N-tris(hydroxymethyl)methyl-3-aminopropanesulfonic acid) and 30 mM HEPES (4-(2-hydroxyethyl)-1-piperazineethanesulfonic acid) (pH=9.2; conductivity: 7770 µS/cm) (E5 to E7);

Counter flow medium: 250 mM mannitol in water (CF1-CF3).

Figure 3:
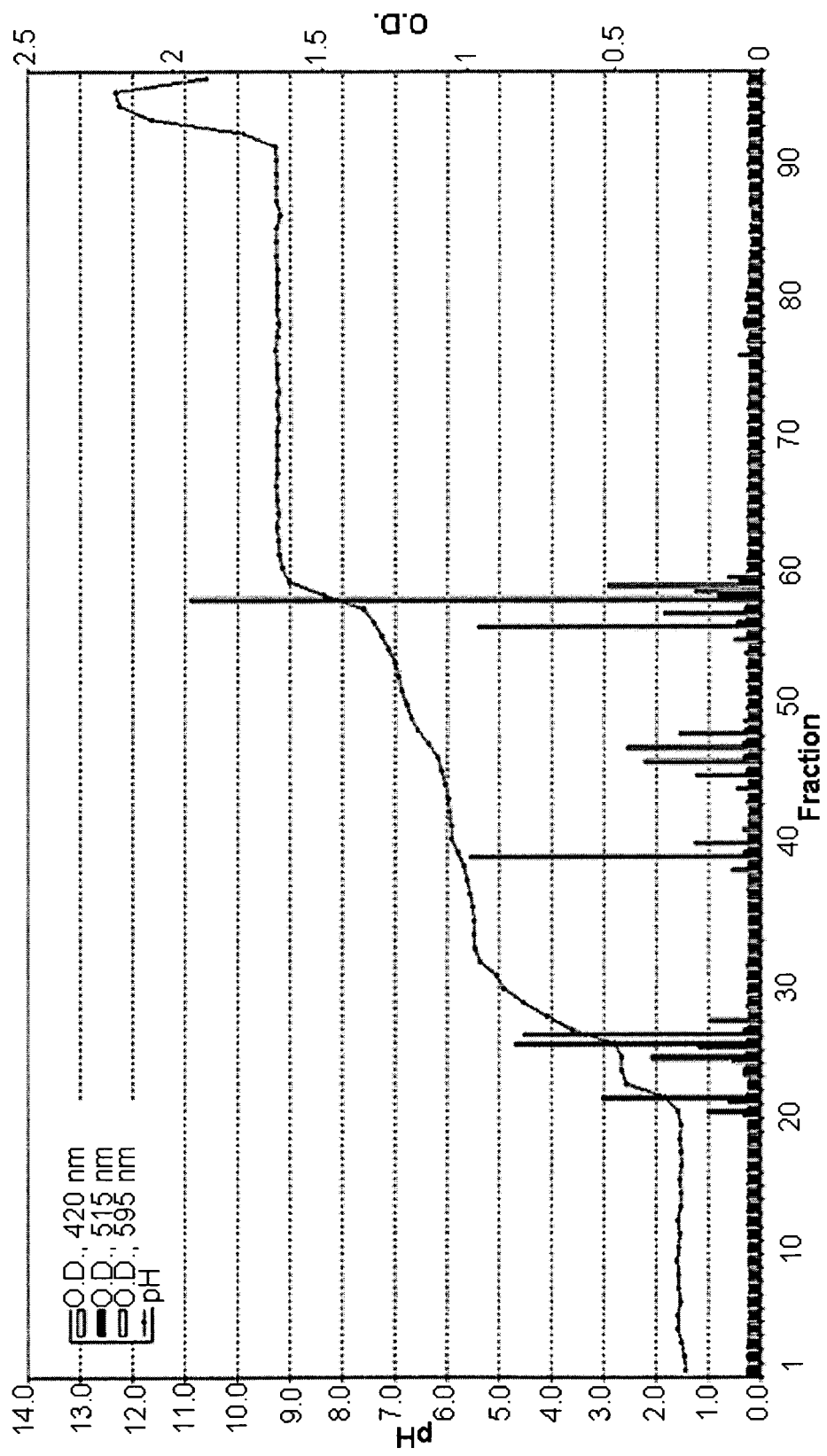
FIG. 3: The absorbance of the FFE fractions at $\lambda=420$ nm, 515 nm, and 595 nm which visualize the distribution of the respective pI-markers of the buffer system comprising 0.1% PPS within the separation zone.
Figure 4:
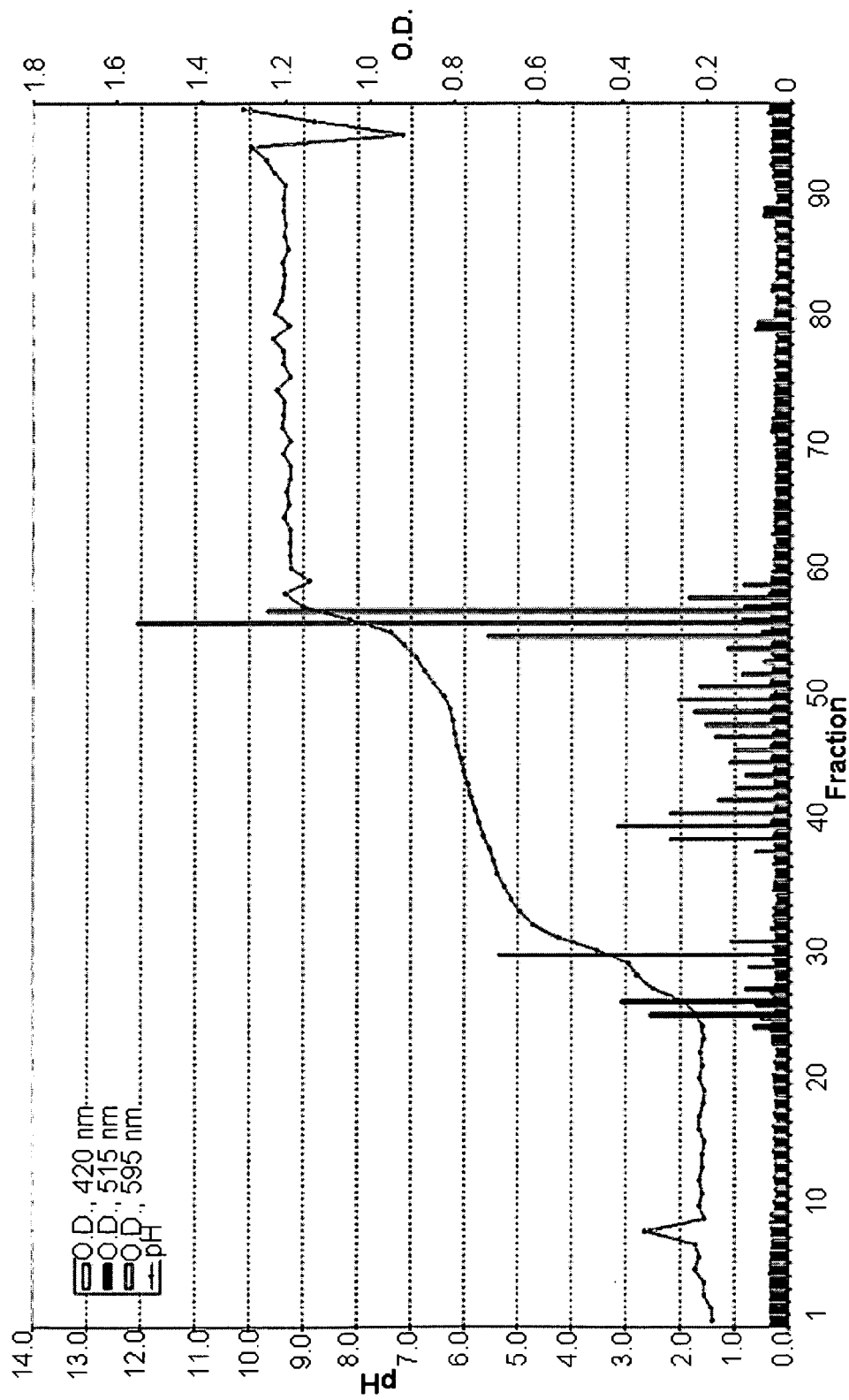
FIG. 4: The absorbance of the FFE fractions at $\lambda=420$ nm, 515 nm, and 595 nm which represent the distribution of the respective pI-markers of the buffer system without 0.1% PPS within the separation zone.

The pH of each of the FFE fractions was determined using a pH electrode and is presented by the graph in FIGS. 3 and 4. Colored pI-markers were separated to evaluate the separation performance of the buffer system of the complementary multi-pair buffer system with and without additional PPS. No significant difference between the pH curves or in the separation pattern of the colored pI-markers was observed. The absorbance of the fraction at λ=420 nm, 515 nm, and 595 nm which represent the absorbance of the respective pI-markers of the buffer system comprising 0.1% PPS are reported in FIG. 3. FIG. 4 shows the pI marker absorbance distribution for the buffer system without PPS.

To demonstrate the identification of proteins after free-flow electrophoresis comprising the use of PPS and complementary multiple pair buffer systems, fractions of the PPS-containing sample were digested and then subjected to LC-MS/MS analysis.

To 150 µl of each separated fraction TCEP (Tris(2-carboxyethyl)phosphine hydrochloride) was added to a final concentration of 5 mM (incubation for 60 min), then IAA (iodoacetamide) was added to a final concentration of 15 mM (incubation 60 min). 5 µg Trypsin (modified, sequencing grade, Promega) was added and the mixtures were incubated over night 37° C. The digestion was stopped by acidifying the solution with 200 mM HCl.

8 µl of each digestion mixture were taken without purification or sample concentration to perform HPLC-MS/MS.

ESI based LC-MS/MS (HCTultra, Bruker, Germany) analyses were carried out using a 75 µm×15 cm fused silica micro capillary reversed phase column (Agilent, USA). Sample volumes were loaded onto a pre-column (reversed phase (C18) column, Agilent, USA). After sample loading, the sample was analyzed at a 200 nl/min flow rate with a gradient of 2% B to 40% B over 30 min. The column was directly coupled to the spray needle (New Objective, USA).

Mobile phase A was 0.1% formic acid and mobile phase B was 100% acetonitrile containing 0.1% formic acid. Peptides eluting from the capillary column were selected for CID by the mass spectrometer using a protocol that alternated between one MS scan (300-1500 m/z) and 3 MS/MS scans. The 3 most abundant precursor ions in each survey scan were selected for CID if the intensity of the precursor ion peak exceeded 10000 ion counts. The electro spray voltage was set to 1.8 kV and the specific m/z value of the peptide fragmented by CID was excluded from reanalysis for 2 min. Mass spectrometer scan functions and HPLC solvent gradients were controlled by the HyStar version 3.2 data system (Bruker, Germany).

Each MS/MS spectrum was searched against the IPI Human database, release no. 3.18, using the Mascot Software (Matrix Science Ltd., U.K.). The probability score calculated by the software was used as the criterion for correct identification. An expectation value of less than 0.05 was required for identification. The ion score of individual peptides was required to be higher than 15. In addition, peptides were required to be fully tryptic with one internal missed cleavage site allowed. Methionine oxidation was included as a variable modification and mass tolerances were 1.5 Da for MS and 0.5 Da for MS/MS. Proteins with at least one peptide passing these criteria were accepted as a possible identification.

As shown in Table 1, the identification of proteins in the presence of PPS and complementary multi pair buffer system using LC-MS/MS was successful.

TABLE 1

Identified proteins in fraction 28, 30, 40 and 48 using
LC-MS/MS in combination with free-flow electrophoresis.

| Fraction | Peptide | Mascot Score | MS Coverage | Protein MW |
|---|---|---|---|---|
| 28 | Tubulin alpha-6 chain | 423 | 16 | 50548.00 |
| | Annexin A1 | 234 | 12 | 38787 |
| | Hypothetical protein DKFZp761K0511 | 219 | 7 | 85189 |
| | Heat shock protein HSP 90-alpha 2 | 203 | 4 | 98622 |
| | Enolase 1 | 194 | 9 | 47481 |
| | 14-3-3 protein zeta/delta | 162 | 14 | 27899 |
| | Isoform Mitochondrial of Peroxiredoxin-5, mitoch | 145 | 18 | 22298 |
| | Isoform 2 of L-lactate dehydrogenase A chain | 124 | 10 | 36953 |
| | L-lactate dehydrogenase B chain | 119 | 4 | 36769 |
| | annexin A2 isoform 1 | 91 | 4 | 40671 |
| | Peroxiredoxin-6 | 82 | 5 | 25002 |
| | tyrosine 3-monooxygenase/tryptophan 5-monooxygen | 80 | 8 | 28179 |
| | 14-3-3 protein epsilon | 77 | 7 | 29326 |
| | NEDD8-conjugating enzyme Ubc12 | 74 | 8 | 21172 |
| | Stress-70 protein, mitochondrial precursor | 73 | 2 | 73920 |
| | PREDICTED: similar to actin, alpha 2, smooth mus | 72 | 6 | 21340 |
| | Prothymosin alpha | 71 | 12 | 12196 |
| | 14-3-3 protein gamma | 66 | 8 | 28325 |
| | Chloride intracellular channel protein 1 | 59 | 20 | 27117 |
| | Aldo-keto reductase family 1 member C3 | 58 | 6 | 37220 |
| | Endoplasmin precursor | 57 | 1 | 92696 |
| | Isoform 2 of Triosephosphate isomerase | 54 | 8 | 27320 |
| | Elongation factor 2 | 52 | 2 | 96115 |
| | PREDICTED: similar to protein disulfide isomeras | 52 | 28 | 5539 |
| | Endoplasmic reticulum protein ERp29 precursor | 47 | 5 | 29032 |
| | Proliferation-associated protein 2G4 | 47 | 4 | 43970 |
| | Fascin | 46 | 2 | 54992 |
| | Transgelin-2 | 45 | 7 | 22417 |
| | ACTA2 protein (Fragment) | 43 | 3 | 37125 |
| 30 | heat shock 70 kDa protein 1A | 369 | 11 | 70280.00 |
| | Tubulin beta-2 chain | 323 | 9 | 50095 |
| | Tubulin beta-2C chain | 305 | 9 | 50255 |
| | Isoform 1 of Carbamoyl-phosphate synthase | 260 | 3 | 165975 |
| | Heat shock protein 60 | 247 | 9 | 61346 |
| | enolase 1 | 231 | 11 | 47481 |
| | Actin, cytoplasmic 1 | 210 | 16 | 42052 |
| | pyruvate kinase 3 isoform 1 | 198 | 13 | 58470 |
| | lactate dehydrogenase A | 184 | 16 | 36950 |
| | Heat-shock protein beta-1 | 184 | 30 | 22826 |
| | 14-3-3 protein sigma | 170 | 20 | 27871 |
| | Isoform 1 of Heat shock cognate 71 kDa protein | 161 | 6 | 71082 |
| | Protein S100-A11 | 140 | 23 | 11847 |
| | Importin beta-1 subunit | 138 | 2 | 98420 |
| | 29 kDa protein | 136 | 9 | 29346 |
| | Elongation factor 2 | 133 | 3 | 96115 |
| | Fatty acid synthase | 132 | 2 | 275850 |
| | heterogeneous nuclear ribonucleoprotein F | 126 | 8 | 45985 |
| | Chloride intracellular channel protein 1 | 120 | 20 | 27117 |
| | Transketolase | 105 | 4 | 68519 |
| | Stathmin-2 | 101 | 10 | 20929 |
| | Desmin | 99 | 4 | 53429 |
| | Phosphoglycerate kinase 1 | 95 | 4 | 44854 |
| | 14-3-3 protein theta | 93 | 8 | 28032 |
| | T-complex protein 1 subunit epsilon | 88 | 3 | 60089 |
| | Hypothetical protein DKFZp761K0511 | 87 | 3 | 85189 |
| | 10 kDa heat shock protein, mitochondrial | 87 | 11 | 10794 |
| | Annexin A1 | 86 | 4 | 38787 |
| | Cofilin-1 | 86 | 8 | 18588 |
| | eukaryotic translation initiation factor 4B | 85 | 2 | 69167 |
| | heterogeneous nuclear ribonucleoprotein H1 | 84 | 7 | 49484 |
| | Glyceraldehyde-3-phosphate dehydrogenase | 83 | 4 | 36070 |
| | 55 kDa protein | 80 | 5 | 55328 |
| | Proteasome activator complex subunit 2 | 76 | 5 | 27384 |
| | tyrosine 3-monooxygenase/tryptophan 5-monooxygen | 76 | 5 | 28179 |
| | Tropomyosin 4 | 72 | 9 | 28619 |
| | Tu translation elongation factor, mitochondrial | 69 | 4 | 50185 |
| | Peptidyl-prolyl cis-trans isomerase A | 66 | 9 | 18098 |
| | Superoxide dismutase | 65 | 8 | 16340 |
| | 14-3-3 protein zeta/delta | 63 | 4 | 27899 |
| | Phosphoglycerate mutase 2 | 62 | 5 | 28788 |
| | Programmed cell death 5 short isoform | 61 | 32 | 4472 |
| | Talin-1 | 60 | 0 | 273171 |
| | Superoxide dismutase [Mn], mitochondrial precurs | 58 | 6 | 24878 |
| | PREDICTED: similar to Heterogeneous nuclear ribo | 57 | 3 | 26578 |

TABLE 1-continued

Identified proteins in fraction 28, 30, 40 and 48 using
LC-MS/MS in combination with free-flow electrophoresis.

| Fraction | Peptide | Mascot Score | MS Coverage | Protein MW |
|---|---|---|---|---|
| | Isoform Long of Trifunctional purine biosyntheti | 55 | 1 | 108953 |
| | Protein S100-A6 | 53 | 8 | 10230 |
| | Isoform Mitochondrial of Peroxiredoxin-5, mitoch | 53 | 12 | 22298 |
| | Transgelin-2 | 52 | 11 | 22417 |
| | L-lactate dehydrogenase B chain | 51 | 5 | 36769 |
| | Acetyl-CoA carboxylase 1 | 51 | 0 | 266469 |
| | Isoform 1 of Nicotinamide phosphoribosyltransfer | 46 | 5 | 55772 |
| | Isoform 1 of Protein SET | 46 | 4 | 33469 |
| | Protein disulfide-isomerase precursor | 45 | 2 | 57480 |
| | Fructose-bisphosphate aldolase C | 43 | 7 | 39699 |
| | FRUCTOSE-BISPHOSPHATE ALDOLASE C | 42 | 3 | 0 |
| | Thymosin beta-10 | 41 | 18 | 4892 |
| | Nucleoside diphosphate kinase B | 41 | 12 | 17401 |
| 40 | Gamma-enolase | 109 | 4 | 47450.00 |
| | Transketolase | 99 | 7 | 68519 |
| | Transitional endoplasmic reticulum ATPase | 95 | 2 | 89819 |
| | Tubulin beta-2C chain | 94 | 11 | 50255 |
| | pyruvate kinase 3 isoform 1 | 88 | 8 | 58470 |
| | Isoform 1 of Heterogeneous nuclear ribonucleopro | 78 | 3 | 51230 |
| | Thioredoxin domain-containing protein 5 precurso | 76 | 4 | 48283 |
| | Calreticulin precursor | 75 | 8 | 48283 |
| | Fatty acid synthase | 73 | 1 | 275850 |
| | Tropomyosin 4 | 73 | 4 | 28619 |
| | T-complex protein 1 subunit delta | 68 | 2 | 58270 |
| | PREDICTED: similar to Ran-specific GTPase-activa | 64 | 7 | 35344 |
| | T-complex protein 1 subunit eta | 61 | 4 | 59842 |
| | thymosin-like 3 | 51 | 29 | 5060 |
| | Thymosin beta-10 | 51 | 30 | 4892 |
| | Actin, aortic smooth muscle | 46 | 3 | 42381 |
| | Acetyl-CoA acetyltransferase, cytosolic | 45 | 6 | 41838 |
| | Glucosidase 2 beta subunit precursor | 45 | 2 | 60228 |
| | Phosphoglycerate kinase 1 | 44 | 5 | 44854 |
| | Semaphorin-3A precursor | 41 | 1 | 89916 |
| | Transgelin-2 | 41 | 11 | 22417 |
| 48 | Triosephosphate isomerase | 250 | 15 | 30802.00 |
| | Thioredoxin domain-containing protein 5 precurso | 145 | 7 | 48283 |
| | Stress-70 protein, mitochondrial precursor | 132 | 4 | 73920 |
| | Heat shock 70 kDa protein 1 | 119 | 3 | 70294 |
| | Hypothetical protein | 108 | 2 | 72492 |
| | Phosphoglycerate kinase 1 | 106 | 6 | 44854 |
| | Actin, cytoplasmic 1 | 95 | 9 | 42052 |
| | Programmed cell death protein 5 | 93 | 10 | 14145 |
| | Annexin A1 | 90 | 4 | 38787 |
| | Stathmin | 87 | 16 | 17161 |
| | T-complex protein 1 subunit delta | 82 | 2 | 58270 |
| | TUBA6 protein | 80 | 11 | 37681 |
| | Tryptophanyl-tRNA synthetase | 79 | 3 | 53474 |
| | Nuclear migration protein nudC | 76 | 3 | 38276 |
| | Isoform 5 of Dynamin-1-like protein | 76 | 3 | 79587 |
| | Fatty acid synthase | 73 | 0 | 275850 |
| | Annexin A5 | 70 | 3 | 35840 |
| | Endoplasmin precursor | 70 | 1 | 92696 |
| | Isoform 1 of Cyclin-dependent kinase inhibitor 2 | 70 | 7 | 16579 |
| | Elongation factor 2 | 66 | 1 | 96115 |
| | Isoform 1 of Carbamoyl-phosphate synthase [ammon | 66 | 0 | 165975 |
| | Isocitrate dehydrogenase [NADP] cytoplasmic | 66 | 3 | 46915 |
| | Malate dehydrogenase, mitochondrial precursor | 65 | 6 | 35965 |
| | Rab GDP dissociation inhibitor alpha | 65 | 4 | 51177 |
| | Flavin reductase | 62 | 4 | 22751 |
| | Alpha-actinin-4 | 62 | 1 | 105245 |
| | 14-3-3 protein gamma | 59 | 4 | 28325 |
| | Protein S100-A11 | 57 | 10 | 11847 |
| | Hypothetical protein DKFZp761K0511 | 54 | 2 | 85189 |
| | Glutathione transferase omega-1 | 54 | 4 | 27833 |
| | Isoform 2 of Neutral alpha-glucosidase AB precur | 50 | 1 | 109825 |
| | 14 kDa protein | 50 | 7 | 13781 |
| | Elongation factor 1-gamma | 49 | 3 | 50298 |
| | Isoform 1 of Heterogeneous nuclear ribonucleopro | 49 | 2 | 51230 |
| | Isoform 1 of Plectin-1 | 49 | 0 | 533408 |
| | Isoform DFF45 of DNA fragmentation factor alpha | 49 | 5 | 36899 |
| | DNA-(apurinic or apyrimidinic site) lyase | 49 | 5 | 35800 |
| | Proliferating cell nuclear antigen | 48 | 5 | 29092 |
| | Zinc finger protein 313 | 48 | 5 | 26647 |
| | T-complex protein 1 subunit theta | 47 | 1 | 60311 |

TABLE 1-continued

Identified proteins in fraction 28, 30, 40 and 48 using
LC-MS/MS in combination with free-flow electrophoresis.

| Fraction Peptide | Mascot Score | MS Coverage | Protein MW |
|---|---|---|---|
| Protein S100-A9 | 45 | 11 | 13291 |
| plastin 3 | 45 | 2 | 71279 |
| Similar to Actin, cytoplasmic 1 | 44 | 7 | 22865 |
| Isoform Beta of Heat-shock protein 105 kDa | 43 | 1 | 92970 |
| Tubulin beta-2C chain | 43 | 3 | 50255 |
| PREDICTED: similar to SMT3 suppressor of mif two | 43 | 6 | 18200 |
| Stress-induced-phosphoprotein 1 | 42 | 2 | 63227 |
| F-actin capping protein alpha-1 subunit | 41 | 7 | 32942 |
| Sorting nexin-5 | 41 | 2 | 47072 |
| CDNA FLJ45525 fis, clone BRTHA2026311, highly si | 41 | 2 | 54408 |
| Transketolase | 40 | 1 | 68519 |
| 60S acidic ribosomal protein P0 | 40 | 3 | 34423 |
| Histone-binding protein RBBP4 | 40 | 2 | 47780 |

Example 3

Separation and Identification of Membrane Proteins from HELA Cells using PPS In a first step, samples of a total cell extraction and of a membrane protein extraction in the presence of PPS were prepared.

To prepare a sample of a total cell extract (solution comprising soluble proteins and membrane proteins), $10^8$ HeLa cells were sonicated in 1.5 ml HBS-buffer+4% PPS (3-3[-(1,1-bisalkyloxyethyl)pyridine-1-yl]propane-1-sulfonate)+1 µl benzonase. The sample was centrifuged (6000 g) and the supernatant was recovered for FFE separation.

To prepare a sample of a membrane protein extraction, $10^8$ HeLa cells were sonicated in 1.5 ml HBS-buffer+1 µl benzonase and centrifuged (6000 g). The supernatant was collected and additional 1.5 ml HBS-buffer was added to the pellet that was sonicated and centrifuged at 600 g. The supernatants were combined and ultracentrifuged (125000 g). The pellet was resuspended in $Na_2CO_3$-buffer (final protein concentration 1 mg/ml), incubated on ice for 30 min and ultracentrifuged (125000 g). The pellets were washed one time with HBS-buffer and ultracentrifuged again. The pellets were resuspended in HBS-buffer containing 4% PPS (3-3[-(1,1-bisalkyloxyethyl)pyridine-1-yl]propane-1-sulfonate), sonicated, incubated on ice for 20 min and ultracentrifuged. The supernatant was collected and prepared for FFE separation.

Interval zone free-flow electrophoresis (IZE) was carried out on a BD™ Free-flow Electrophoresis System in cyclic interval modus. The apparatus was set up comprising seven media inlets (E1-E7) and four sample inlets (S1-S4). Anodic stabilizing medium was introduced into inlet E1. The cathodic stabilizing medium was introduced into inlet E7 and the sample was introduced via sample inlet S3. The buffer system used herein was an A/B medium as described above. The voltage applied was 950 V and the current was 50 mA. The sample and the media were introduced at a flow rate of 2.5 ml/h and 250 ml/h, respectively. Media flow rate during interval was 90 ml/h and during collection of the fractions 300 ml/h, respectively.

Separation and Stabilizing Media within the FFE Apparatus:

| | inlet: | | |
|---|---|---|---|
| | E1 | E2 E3 E4 E5 E6 | E7 |
| pH | 6.57 | 7.66 | 8.92 |
| | 100 mM $H_2SO_4$ | 50 mM Morpholinoethanol | 100 mM NaOH |
| | 50 mM MES | 50 mM TAPS | 50 mM Tris |
| | 250 mM Morpholino-ethanol | 0.1% PPS | 150 mM TAPS |
| Conductivity/ [µS/cm] | 11100 | 369 | 5420 |

Counter flow medium: water

Figure 5:
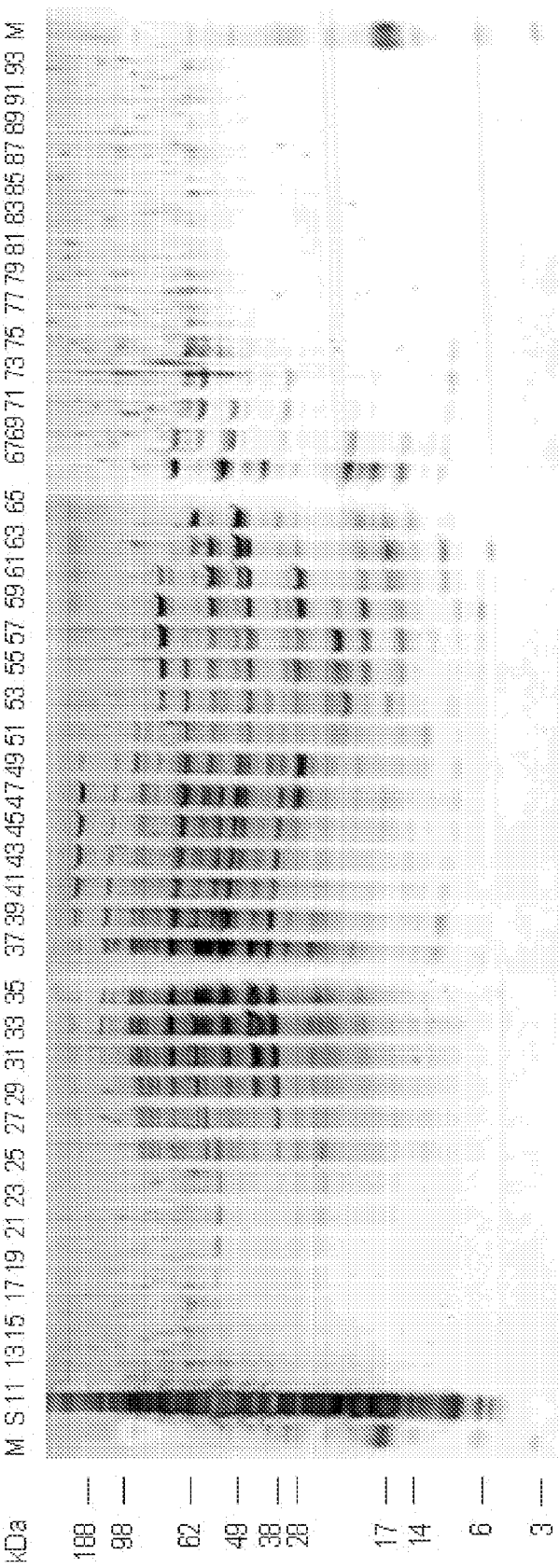
FIG. 5: Silver stained SDS Page of free-flow zone electrophoresis fractions of a sample containing the total cell extract from HELA cells (extracted in HBS buffer with PPS.
Figure 6:
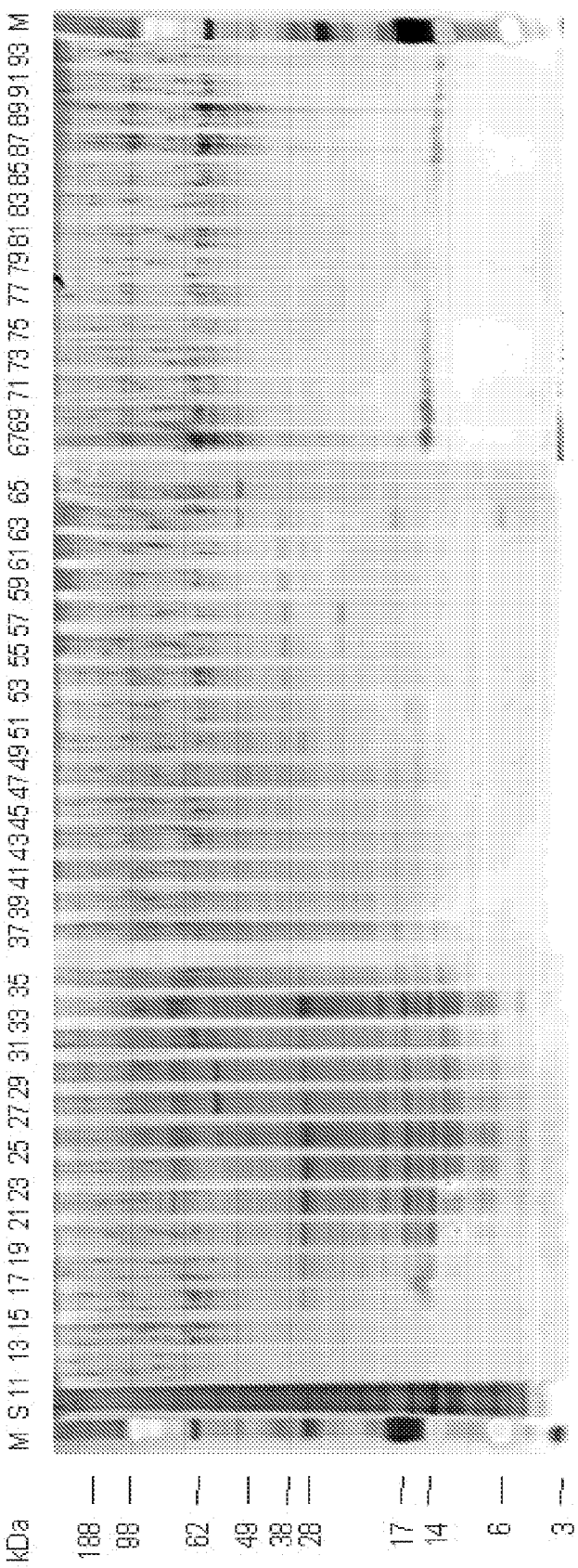
FIG. 6: Silver stained SDS page of free-flow electrophoresis fractions of a sample containing membrane proteins extracted with PPS.

A silver-stained gel of the separated fractions of a sample comprising the total cell extract of HeLa cells that was separated using IZE is shown in FIG. 5. FIG. 6 shows a silver stained gel of the separated fractions of a sample containing the membrane proteins of HeLa cells that were separated using IZE.

The fractions were prepared as described in Example 2 prior to subjecting the separated fractions to LC-MS/MS.

ESI based LC-MS/MS (HCTultra, Bruker, Germany) was carried out as described in Example 2.

Each MS/MS spectrum was searched against the IPI Human database, release no. 3.18, using the Mascot Software (Matrix Science Ltd., U.K.) as described in Example 2.

96 proteins very identified in total from the crude non-separated HeLa membrane protein sample of which 54 were membrane proteins. The identified proteins are summarized in Table 2. As a not limiting example, fraction 22 of the FFE separation was subjected to a mass spectrometric analysis. In total, 15 membrane proteins and 5 cytosolic proteins were identified in fraction 22. The results are summarized in Table 3. Notably, 3 of the 20 proteins identified in fraction 22 of the FFE separation were not identified in the crude non-separated sample. The three additional found proteins are highlighted in bold.

TABLE 2

The 96 identified proteins (54 membrane proteins) of the crude non-separated HeLa membrane protein sample

| Peptide | Mascot Score | MS Coverage | Protein MW | pI-Value | Found Peptides | Nature |
|---|---|---|---|---|---|---|
| solute carrier family 3 (activators of dibasic and neutral amino acid transport), member 2 isoform d | 1042 | 44 | 65003 | 4.8 | 20 | integral (1TM) |
| Voltage-dependent anion-selective channel protein 1 | 546 | 43 | 30737 | 9.27 | 10 | channel protein |
| Isoform Long of Sodium/potassium-transporting ATPase alpha-1 chain precursor | 446 | 9 | 114135 | 5.21 | 6 | multi-pass membrane protein (10TM) |
| HLA class I histocompatibility antigen, A-68 alpha chain precursor | 390 | 31 | 41168 | 6.24 | 7 | single-pass typ I membrane protein (1TM) |
| Glyceraldehyde-3-phosphate dehydrogenase | 373 | 29 | 36070 | 9.3 | 7 | cytoplasmatic |
| Isoform 1 of Voltage-dependent anion-selective channel protein 2 | 323 | 22 | 38639 | 6.37 | 9 | channel protein |
| Isoform GN-1S of Glycogenin-1 | 315 | 27 | 29078 | 4.58 | 6 | cytoplasmatic |
| Interferon-induced transmembrane protein 3 | 292 | 31 | 14794 | 6.62 | 4 | multi-pass memrane protein (3TM) |
| Low-density lipoprotein receptor precursor | 291 | 8 | 98906 | 4.72 | 5 | single-pass typ I membrane protein (1TM) |
| Isoform 2 of Basigin precursor | 274 | 23 | 29431 | 5.32 | 4 | single-pass typ I membrane protein (1TM) |
| Keratin, type II cytoskeletal 1 | 268 | 11 | 66018 | 8.82 | 5 | cytosceletal |
| Brain acid soluble protein 1 | 258 | 35 | 22549 | 4.47 | 5 | cytoplasmatic |
| Actin, cytoplasmic 1 | 256 | 24 | 42052 | 5.18 | 5 | cytosceletal |
| HLA class I histocompatibility antigen, Cw-12 alpha chain precursor | 244 | 21 | 41316 | 5.88 | 5 | single-pass typ I membrane protein (1TM) |
| Prohibitin | 238 | 23 | 29843 | 5.47 | 4 | integral (1TM) |
| CD44 antigen isoform 4 precursor | 237 | 11 | 39904 | 5.09 | 3 | multi-pass membrane protein (6TM) |
| mucin-13 precursor | 210 | 9 | 32971 | 10.27 | 3 | single-pass typ I membrane protein (1TM) |
| integrin beta 1 isoform 1A precursor | 209 | 8 | 91664 | 5.14 | 4 | integral (1TM) |
| enolase 1 | 207 | 10 | 47481 | 7.71 | 3 | cytoplasmatic |
| Ras-related protein Rab-7 | 202 | 22 | 23760 | 7.2 | 3 | cytoplasmatic |
| Keratin, type I cytoskeletal 10 | 195 | 5 | 59711 | 4.99 | 2 | cytosceletal |
| Mucin-13 precursor | 195 | 8 | 55710 | 4.77 | 3 | integral (1TM) |
| Vesicle-associated membrane protein 3 | 192 | 33 | 11228 | 9.7 | 2 | single-pass typ I membrane protein (1TM) |
| CD81 antigen | 184 | 16 | 26476 | 4.95 | 2 | multi-pass membrane protein (4TM) |
| Isoform 1 of Heat shock cognate 71 kDa protein | 182 | 4 | 71082 | 5.24 | 2 | cytoplasmatic |
| Keratin, type I cytoskeletal 9 | 178 | 10 | 62320 | 5.06 | 3 | cytosceletal |
| Vesicle-associated membrane protein 2 | 175 | 28 | 12567 | 9.17 | 3 | single-pass typ IV membrane protein (1TM) |
| Cation-dependent mannose-6-phosphate receptor precursor | 163 | 11 | 31487 | 5.49 | 2 | integral (1TM) |
| Hypothetical protein | 161 | 4 | 72492 | 4.92 | 2 | |
| Isoform 1 of Coxsackievirus and adenovirus receptor precursor | 161 | 13 | 40575 | 8.63 | 4 | single-pass typ I membrane protein (1TM) |
| Ephrin type-A receptor 2 precursor | 156 | 3 | 109667 | 5.76 | 2 | integral (1TM) |
| Isoform D of Plasma membrane calcium-transporting ATPase 1 | 150 | 3 | 139637 | 5.67 | 3 | multi-pass membrane protein (10) |
| Neutral amino acid transporter B(0) | 144 | 9 | 57018 | 5.22 | 3 | multi-pass membrane protein (10) |
| Isoform 1 of Probable mitochondrial import receptor subunit TOM40 homolog | 142 | 16 | 38211 | 6.97 | 3 | multi-pass membrane protein |
| TUBA6 protein | 137 | 16 | 37681 | 9.54 | 3 | cytoplasmytic |
| Ubiquinol-cytochrome-c reductase complex core protein 2, mitochondrial precursor | 134 | 8 | 48584 | 9.32 | 2 | transitorial |

TABLE 2-continued

The 96 identified proteins (54 membrane proteins) of the crude non-separated HeLa membrane protein sample

| Peptide | Mascot Score | MS Coverage | Protein MW | pI-Value | Found Peptides | Nature |
|---|---|---|---|---|---|---|
| Leucine-rich repeat-containing protein 59 | 128 | 14 | 35308 | 10.36 | 3 | single-pass typ II membrane protein (1TM) |
| Cytochrome c oxidase polypeptide Va, mitochondrial precursor | 125 | 20 | 16935 | 6.38 | 2 | transitorial |
| Isoform 1 of Voltage-dependent anion-selective channel protein 3 | 122 | 20 | 30981 | 9.55 | 4 | channel protein |
| Phosphoglycerate kinase 1 | 118 | 8 | 44854 | 9.21 | 2 | cytoplasmytic |
| Isoform Delta15 of Platelet endothelial cell adhesion molecule precursor | 113 | 7 | 82239 | 6.93 | 3 | |
| Desmoglein 2, preproprotein | 109 | 1 | 123016 | 5 | 1 | single-pass typ I membrane protein (1TM) |
| L-lactate dehydrogenase A-like 6B | 106 | 4 | 42408 | 9.74 | 1 | cytoplasmatic |
| Isoform SNAP-23a of Synaptosomal-associated protein 23 | 102 | 14 | 23682 | 4.74 | 2 | periferal |
| Up-regulated during skeletal muscle growth protein 5 | 101 | 25 | 6510 | 10.25 | 1 | single-pass membrane protein (1TM) |
| ADP-ribosylation factor-like protein 8B | 99 | 21 | 21753 | 9.58 | 2 | |
| Ras-related protein Ral-A | 98 | 14 | 23723 | 7.48 | 2 | periferal |
| Tetraspanin-8 | 96 | 5 | 26711 | 5.36 | 1 | multi-pass membrane protein (4TM) |
| Protein S100-A14 | 88 | 14 | 11826 | 5.04 | 1 | cytoplasmic |
| Proteolipid protein 2 | 87 | 9 | 17022 | 7.75 | 1 | multi-pass membrane protein (4TM) |
| Zinc transporter 1 | 87 | 7 | 56318 | 6.02 | 2 | multi-pass membrane protein (8TM) |
| High-affinity cationic amino acid transporter 1 | 82 | 2 | 68449 | 5.16 | 1 | multi-pass membrane protein (14TM) |
| Isoform 1 of Neural cell adhesion molecule L1 precursor | 81 | 3 | 140885 | 5.81 | 2 | single-pass membrane protein (1TM) |
| Large neutral amino acids transporter small subunit 1 | 80 | 3 | 55659 | 8.96 | 1 | multi-pass membrane protein (12) |
| Cytochrome c oxidase polypeptide Vb, mitochondrial precursor | 78 | 24 | 13915 | 10.19 | 2 | transitorial |
| Sodium/potassium-transporting ATPase subunit beta-3 | 76 | 5 | 31834 | 9.31 | 1 | single-pass typ II membrane protein (1TM) |
| Isoform 1 of Reticulon-4 | 76 | 4 | 130420 | 4.28 | 2 | multi-pass membrane protein (2TM) |
| Putative S100 calcium-binding protein H_NH0456N16.1 | 76 | 15 | 11673 | 9.75 | 2 | |
| Calnexin precursor | 72 | 2 | 67982 | 4.31 | 1 | single-pass typ I membrane protein (1TM) |
| Vesicular integral-membrane protein VIP36 precursor | 71 | 10 | 40545 | 6.51 | 2 | single-pass typ I membrane protein (1TM) |
| Isoform Sap-mu-0 of Proactivator polypeptide precursor | 70 | 2 | 59899 | 4.93 | 1 | |
| Ras-related protein Rab-2A | 69 | 6 | 23702 | 6.09 | 1 | periferal |
| Heat shock protein HSP 90-alpha 2 | 69 | 1 | 98622 | 4.95 | 1 | cytoplasmic |
| Fructose-bisphosphate aldolase A | 68 | 8 | 39720 | 9.24 | 2 | cytoplasmic |
| Tubulin beta-2 chain | 68 | 6 | 50095 | 4.64 | 2 | cytosceletal |
| Transthyretin precursor | 68 | 15 | 15991 | 5.43 | 1 | seceted |
| SMARCA4 isoform 2 | 67 | 0 | 188658 | 8.9 | 1 | transitorial |
| Ubiquinol-cytochrome c reductase complex 14 kDa protein | 67 | 11 | 13391 | 9.32 | 1 | integral (1TM) |
| Lysosome membrane protein 2 | 67 | 8 | 54581 | 4.86 | 2 | multi-pass membrane protein (2TM) |
| myelin protein zero-like 1 isoform a | 67 | 5 | 29235 | 9.48 | 1 | single-pass typ I membrane protein (1TM) |
| 21 kDa protein | 66 | 7 | 21711 | 9.81 | 2 | |
| ATP synthase e chain, mitochondrial | 63 | 20 | 7797 | 9.55 | 1 | F0 peptide |

TABLE 2-continued

The 96 identified proteins (54 membrane proteins) of the crude non-separated HeLa membrane protein sample

| Peptide | Mascot Score | MS Coverage | Protein MW | pI-Value | Found Peptides | Nature |
|---|---|---|---|---|---|---|
| Heat shock 70 kDa protein 1 | 63 | 4 | 70294 | 5.36 | 2 | |
| Trophoblast glycoprotein precursor | 63 | 4 | 46573 | 6.39 | 1 | single-pass typ I membrane protein (1TM) |
| pyruvate kinase 3 isoform 1 | 61 | 4 | 58470 | 8.97 | 1 | cytoplsmic |
| Isoform A of Phosphate carrier protein, mitochondrial precursor | 59 | 3 | 40525 | 10.1 | 1 | multi-pass membrane protein (6TM) |
| Isoform Long of Endoglin precursor | 58 | 4 | 71559 | 6.15 | 2 | single-pass typ I membrane protein (1TM) |
| Transferrin receptor protein 1 | 58 | 2 | 85274 | 6.18 | 1 | single-pass membrane protein typ II (1TM) |
| Galectin-3 | 56 | 6 | 26098 | 9.2 | 1 | nucleolus |
| Pituitary tumor-transforming gene 1 protein-interacting protein precursor | 54 | 10 | 21109 | 10.68 | 1 | integral (1TM) |
| Elongation factor 2 | 53 | 1 | 96115 | 6.42 | 1 | cytoplasmic |
| Isoform 2 of Guanine nucleotide-binding protein G(i), alpha-2 subunit | 52 | 8 | 39075 | 5.16 | 1 | periferal |
| Hypothetical protein FLJ20455 | 52 | 7 | 27780 | 7.76 | 1 | |
| Isoform Long of Heterogenous nuclear ribonucleoprotein U | 51 | 1 | 91033 | 5.68 | 2 | |
| Prostaglandin F2 receptor negative regulator precursor | 47 | 1 | 99464 | 6.16 | 1 | single-pass typ I membrane protein (1TM) |
| Isoform 1 of Translocon-associated protein alpha subunit precursor | 47 | 5 | 32215 | 4.22 | 2 | single-pass typ I membrane protein (1TM) |
| UDP-Gal:betaGlcNAc beta 1,4-galactosyltransferase 1, membrane-bound form | 47 | 3 | 44291 | 9.6 | 1 | single-pass typ II membrane protein (1TM) |
| golgi phosphoprotein 4 | 46 | 1 | 81888 | 4.58 | 1 | single-pass typ II membrane protein (1TM) |
| cytochrome b5 reductase isoform 1 | 43 | 6 | 34441 | 7.9 | 2 | periferal |
| Ras-related protein Rab-35 | 43 | 7 | 23296 | 9.42 | 1 | periferal |
| Mitochondrial precursor proteins import receptor | 43 | 2 | 68096 | 6.91 | 1 | intecral (1TM) |
| Histone H4 | 42 | 11 | 11229 | 11.85 | 1 | nucleus |
| Isoform 1 of Choline transporter-like protein 2 | 42 | 2 | 81638 | 9.8 | 1 | multi-pass membrane protein (10TM) |
| Calmodulin | 40 | 11 | 16696 | 3.93 | 1 | cytoplasmic |
| synaptobrevin-like 1 | 40 | 8 | 25261 | 9.73 | 1 | single-pass typ IV membrane protein (1TM) |
| cytochrome b5 outer mitochondrial membrane precursor | 40 | 22 | 16798 | 4.73 | 1 | periferal |

TABLE 3

The 20 identified proteins (15 membrane proteins) of fraction 22 of the separated HeLa membrane protein

| Title | Mascot Score | MS Coverage | Protein MW | pI-Value | Found Peptides | Nature |
|---|---|---|---|---|---|---|
| Keratin, type II cytoskeletal 1 | 349 | 9 | 66018 | 8.8 | 6 | cytosceletal |
| Brain acid soluble protein 1 | 312 | 35 | 22549 | 4.47 | 6 | cytoplamsmic |
| Keratin, type I cytoskeletal 10 | 205 | 7 | 59711 | 4.99 | 3 | cytosceletal |
| 4F2 cell-surface antigen heavy chain | 201 | 13 | 58023 | 5.07 | 5 | single-pass typ II membrane protein (1TM) |
| Glyceraldehyde-3-phosphate dehydrogenase | 161 | 17 | 36070 | 9.3 | 4 | cytoplasmatic |
| Low-density lipoprotein receptor precursor | 158 | 3 | 98906 | 4.72 | 2 | single-pass typ I membrane protein (1TM) |
| Voltage-dependent anion-selective channel protein 1 | 130 | 15 | 30737 | 9.27 | 3 | channel protein |

TABLE 3-continued

The 20 identified proteins (15 membrane proteins) of fraction 22 of the separated HeLa membrane protein

| Title | Mascot Score | MS Coverage | Protein MW | pI-Value | Found Peptides | Nature |
|---|---|---|---|---|---|---|
| Isoform 1 of Voltage-dependent anion-selective channel protein 2 | 125 | 12 | 38639 | 6.37 | 4 | channel protein |
| Keratin, type II cytoskeletal 2 epidermal | 91 | 3 | 66111 | 8.85 | 2 | cytosceletal |
| Keratin, type I cytoskeletal 9 | 88 | 2 | 62320 | 5.06 | 1 | cytosceletal |
| Vesicle-associated membrane protein 3 | 81 | 17 | 11228 | 9.7 | 1 | single-pass typ IV membrane protein (1TM) |
| CD44 antigen isoform 4 precursor | 76 | 3 | 39904 | 5.09 | 2 | single-pass typ I membrane protein (1TM) |
| Isoform 2 of Basigin precursor | 75 | 11 | 29431 | 5.32 | 2 | single-pass typ I membrane protein (1TM) |
| Up-regulated during skeletal muscle growth protein 5 | 62 | 25 | 6510 | 10.25 | 1 | single-pass typ I membrane protein (1TM) |
| Neutral amino acid transporter B(0) | 60 | 3 | 57018 | 5.22 | 1 | multi-pass membrane protein 10TM) |
| Cation-dependent mannose-6-phosphate receptor precursor | 55 | 5 | 31487 | 5.49 | 2 | single-pass typ IV membrane protein (1TM) |
| Leucine zipper-EF-hand-containing transmembrane protein 1, mitochondrial precursor | 55 | 1 | 83986 | 6.29 | 1 | integral (1TM) |
| Calnexin precursor | 52 | 2 | 67982 | 4.31 | 1 | single-pass typ I membrane protein (1TM) |
| Integrin alpha-5 precursor | 45 | 1 | 115605 | 5.42 | 1 | single-pass typ I membrane protein (1TM) |
| Interferon-induced transmembrane protein 3 | 43 | 18 | 14794 | 6.62 | 2 | multi-pass membrane protein (3TM) |
| Mucin-13 precursor | 41 | 2 | 55710 | 4.77 | 1 | single-pass typ I membrane protein (1TM) |

As demonstrated herein, FFE separations in accordance with the present invention yields mass spectra having less complexity. Thus, the spectra with reduced complexity allow an easier analysis, and furthermore make the detection of additional signals possible that would otherwise be suppressed in more complex spectra due to, e.g., merely low concentrations of analytes which are responsible for said signals.

Example 4

Separation of Peptides and Identification of Proteins from HELA Cells Prepared with and without PPS A sample of $10^8$ HeLa cells were sonicated in HBS buffer (10 mM HEPES pH 7.9; 1.5 mM $MgCl_2$, 10 mM KCl+ protease inhibitors (1 tablet complete mini, Roche #11836153001 10 ml) and ultracentrifuged at 100 000 g in parallel. The supernatant contained the soluble proteins.

The supernatant was divided into two parts that were treated identically as follows: 100 mM ammonium bicarbonate buffer was added. TCEP was added to a final concentration of 5 mM (incubation for 60 min), then IAA was added to a final concentration of 15 mM (incubation 60 min). Trypsin (modified, sequencing grade, Promega) was added to a final ratio of 1:37.5 enzyme:protein and the mixture was incubated over night at 37° C. The digestion was stopped by acidifying the solution with 0.1% TFA (trifluoracetic acid).

In parallel, the peptides of the two samples were purified using SepPak® Vac 1 cc tC18 cartridges (Waters). The procedure contained washing the cartridge with acetonitrile and 0.1% TFA, loading the sample, washing sample with 0.1% TFA, eluting peptides with acetonitrile, evaporating the samples to dryness by vacuum centrifugation and reconstituting in 1 ml separation medium which was introduced into inlet S2.

The isoelectric focusing was carried out on a BD™ Free-flow Electrophoresis System in FF-IEF static interval mode. The apparatus was set up comprising nine media inlets (E1-E9) and four sample inlets (S1-S4). Anodic stabilizing medium was introduced into inlet E1. The cathodic stabilizing medium was introduced into inlet E9 and the sample was introduced via sample inlet S3. The voltage applied was 500 V and the current was 130 mA. The sample and the media were introduced at a flow rate of 3 ml/h and 150 ml/h, respectively.

Separation and Stabilizing Media within the FFE Apparatus:

| | Media inlet | | | | | | | | |
|---|---|---|---|---|---|---|---|---|---|
| | E1 | E2 | E3 | E4 | E5 | E6 | E7 | E8 | E9 |
| pH | 4.0<br>225 mM Tris, add HAc to pH 4 | 3.9<br>150 mM HAc, 100 mM betaine, 25 mM Tris | 4.8<br>10 mM Tris, add HAc to pH 4.85 | | | 6.47<br>10 mM HAc, add Tris to pH 6.4 | | 7.85<br>150 mM HAc, 150 mM Tris, add Tris to pH 7.8 | 8.16<br>450 mM HAc, 900 mM Tris |
| Conductivity/ [µS/cm] | 6830 | 1605 | 615 | | | 600 | | 6890 | 6020 |

Counter flow medium: water

FFE separations of the two samples were carried out using the setup and media as describe above.

In case of the PPS experiment, PPS was added to the media (E1-E9) of a concentration of 0.1%.

Figure 7:
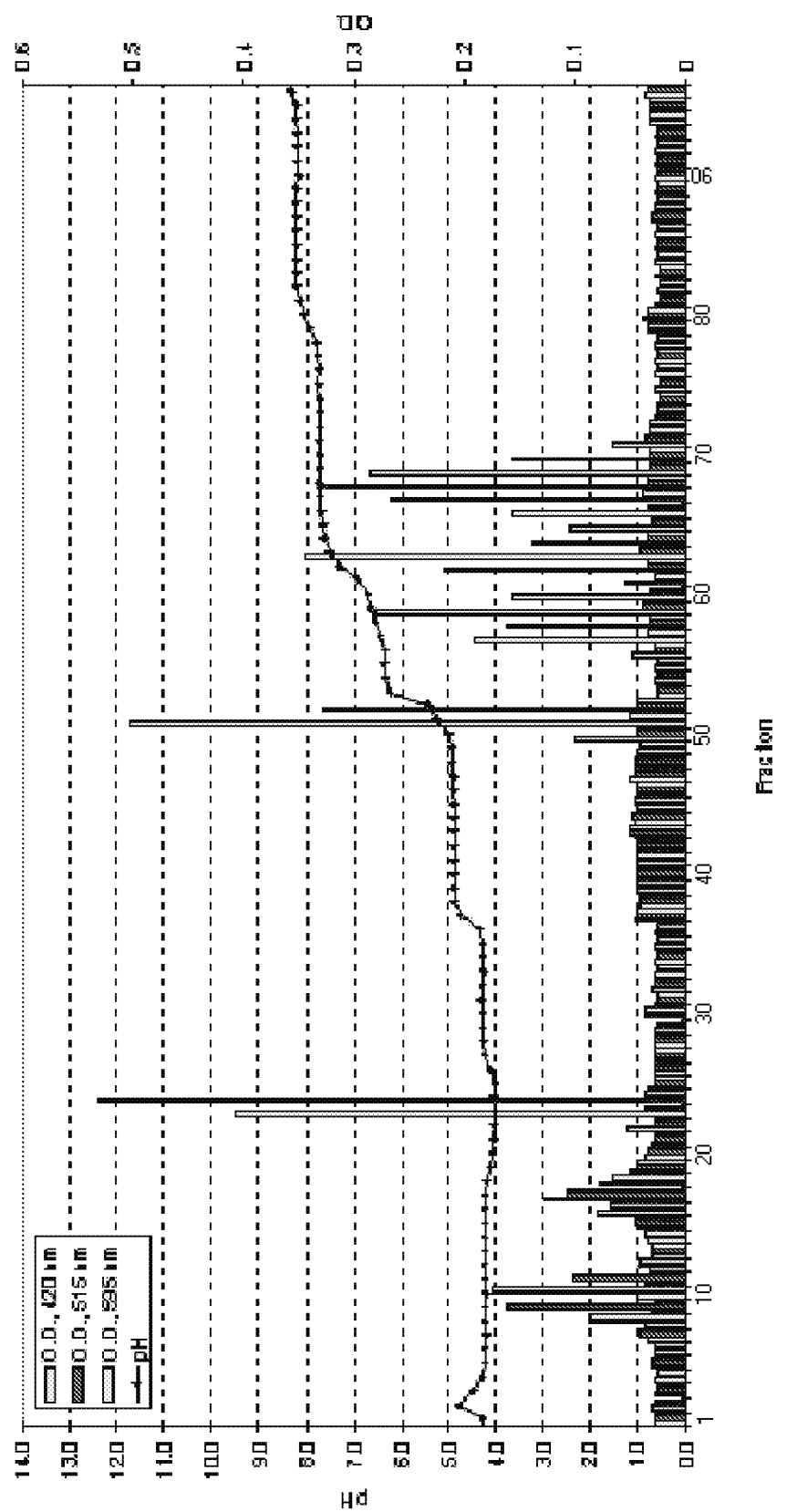
FIG. 7: The FFE separation elution profile represented by the absorbance of the FFE fractions at $\lambda=420$ nm, 515 nm, and 595 nm which visualize the distribution of the respective pI-markers of the buffer system comprising 0.1% PPS within the separation zone.
Figure 8:
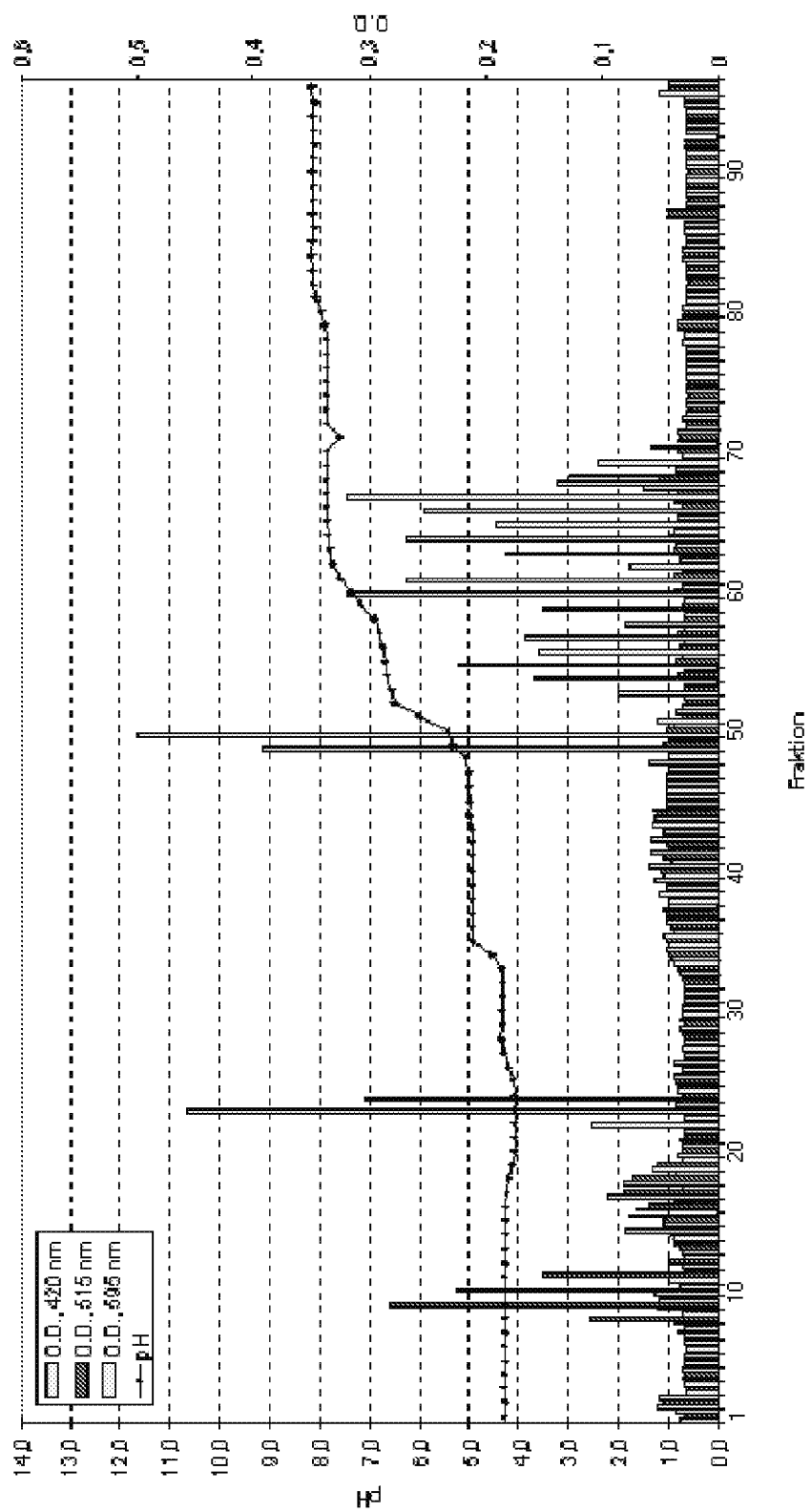
FIG. 8: The FFE separation elution profiles represented by the absorbance of the FFE fractions at $\lambda=420$ nm, 515 nm, and 595 nm which visualize the distribution of the respective pI-markers of the buffer system without PPS within the separation zone.

The FFE separation elution profiles with and without PPS are shown in FIG. 7 and FIG. 8, respectively.

100 µl of each fraction of the FFE separations were evaporated to dryness using a SpeedVac, dissolved in 25 µl 0.1% TFA and 5 µl thereof were used for LC-MS/MS experiments.

Proteins were identified as described in Example 2. Notably, more proteins were identified in fractions of the sample where the separation medium contained PPS. As an example, in fraction 32 of the sample without PPS, 48 different proteins were identified by LC MS/MS whereas in fraction 32 of the experiment containing separation media with PPS, 70 different proteins could be identified. The results of the subsequent LC MS/MS analysis are summarized in Table 4 and Table 5, respectively.

TABLE 4

Protein identification by LC-MS/MS after free-flow isoelectric focusing without PPS

| Fraction | Peptide | Mascot Score | MS Coverage | pI-Value | Protein MW |
|---|---|---|---|---|---|
| 32 | Actin, aortic smooth muscle | 176 | 9 | 5.1 | 42381 |
| | Isoform M1 of Pyruvate kinase isozymes M1/M2 | 159 | 5 | 8.64 | 58407 |
| | TUBA6 protein | 150 | 8 | 9.54 | 37681 |
| | Heat shock protein 60 | 149 | 4 | 5.59 | 61346 |
| | Hypothetical protein DKFZp761K0511 | 146 | 3 | 5.13 | 85189 |
| | FK506-binding protein 4 | 139 | 9 | 5.22 | 51926 |
| | Hsc70-interacting protein | 101 | 3 | 5.04 | 41477 |
| | heat shock 70 kDa protein 4 isoform b | 98 | 16 | 4.46 | 15851 |
| | Nascent polypeptide-associated complex alpha sub | 91 | 6 | 4.36 | 23370 |
| | Elongation factor 2 | 89 | 1 | 6.42 | 96115 |
| | Filamin A, alpha | 88 | 0 | 5.64 | 282581 |
| | 14-3-3 protein gamma | 86 | 5 | 4.65 | 28325 |
| | 29 kDa protein | 85 | 8 | 4.6 | 29346 |
| | 46 kDa protein | 82 | 3 | 4.63 | 46713 |
| | T-complex protein 1 subunit beta | 82 | 2 | 6 | 57663 |
| | Annexin A1 | 82 | 3 | 6.68 | 38787 |
| | D-3-phosphoglycerate dehydrogenase | 79 | 2 | 6.31 | 57225 |
| | Thioredoxin | 79 | 12 | 4.67 | 11884 |
| | 14-3-3 protein sigma | 78 | 5 | 4.53 | 27871 |
| | Alpha-actinin-1 | 77 | 1 | 5.13 | 103563 |
| | Isoform 1 of Exportin-2 | 74 | 1 | 5.43 | 111145 |
| | Heat shock 70 kDa protein 7 (Fragment) | 70 | 6 | 7.77 | 27004 |
| | Hypothetical protein | 69 | 1 | 4.92 | 72492 |
| | Isoform 1 of Eukaryotic translation initiation f | 69 | 1 | 4.74 | 92833 |
| | lactate dehydrogenase A | 66 | 3 | 9.26 | 36950 |
| | Transketolase | 65 | 3 | 8.54 | 68519 |
| | Isoform 1 of Neutral alpha-glucosidase AB precur | 65 | 3 | 5.7 | 107263 |
| | Isoform 1 of Heat shock cognate 71 kDa protein | 64 | 2 | 5.24 | 71082 |
| | Calreticulin precursor | 64 | 5 | 4.14 | 48283 |
| | Lupus La protein | 63 | 2 | 6.8 | 46979 |
| | Keratin, type II cytoskeletal 8 | 63 | 4 | 5.38 | 53540 |
| | Isoform 1 of Heterogeneous nuclear ribonucleopro | 61 | 3 | 8.52 | 38581 |
| | Eukaryotic translation initiation factor 2 subun | 61 | 3 | 9.57 | 51516 |
| | Phosphoglycerate kinase 1 | 60 | 2 | 9.21 | 44854 |
| | Nucleosome assembly protein 1-like 4 | 60 | 2 | 4.45 | 43155 |
| | Fatty acid synthase | 59 | 0 | 5.98 | 275850 |
| | Endoplasmin precursor | 59 | 1 | 4.61 | 92696 |
| | hydroxyacyl-Coenzyme A dehydrogenase, type II is | 58 | 6 | 9.06 | 27134 |
| | Isoform 1 of Protein SET | 58 | 3 | 4.07 | 33469 |
| | Ribonuclease inhibitor | 56 | 3 | 4.56 | 51635 |
| | DNA replication licensing factor MCM6 | 51 | 1 | 5.16 | 93801 |
| | GARS protein | 50 | 1 | 8.75 | 85336 |
| | GARS PROTEIN | 48 | 1 | 5.5 | 0 |

TABLE 4-continued

Protein identification by LC-MS/MS after free-flow isoelectric focusing without PPS

| Fraction | Peptide | Mascot Score | MS Coverage | pI-Value | Protein MW |
|---|---|---|---|---|---|
| | Chromobox protein homolog 3 | 45 | 7 | 5.08 | 20981 |
| | Annexin A5 | 45 | 3 | 4.78 | 35840 |
| | DnaJ homolog subfamily C member 7 | 43 | 2 | 6.62 | 57203 |
| | Nucleosome assembly protein 1-like 1 | 42 | 4 | 4.21 | 45631 |
| | 132 kDa protein | 39 | 1 | 4.73 | 132516 |
| 42 | Isoform 1 of Heat shock cognate 71 kDa protein | 306 | 9 | 5.2 | 71082 |
| | heat shock 70 kDa protein 1A | 253 | 5 | 5.35 | 70280 |
| | Hypothetical protein | 230 | 6 | 4.92 | 72492 |
| | Stress-70 protein, mitochondrial precursor | 188 | 4 | 5.81 | 73920 |
| | Filamin A, alpha | 165 | 1 | 5.64 | 282581 |
| | Actin, cytoplasmic 1 | 163 | 11 | 5.18 | 42052 |
| | Cofilin-1 | 144 | 15 | 9.19 | 18588 |
| | Isoform 1 of Carbamoyl-phosphate synthase [ammon | 122 | 1 | 6.3 | 165975 |
| | eukaryotic translation initiation factor 4B | 114 | 5 | 5.41 | 69167 |
| | Glucose-6-phosphate isomerase | 102 | 2 | 9.14 | 63204 |
| | Ubiquitin-activating enzyme E1 | 97 | 2 | 5.8 | 57443 |
| | Isoform M1 of Pyruvate kinase isozymes M1/M2 | 90 | 3 | 8.64 | 58407 |
| | Elongation factor 1-delta | 89 | 4 | 4.75 | 31086 |
| | Fructose-bisphosphate aldolase A | 86 | 3 | 9.24 | 39720 |
| | Thioredoxin-like protein 5 | 86 | 11 | 5.27 | 14217 |
| | lactate dehydrogenase A | 86 | 8 | 9.26 | 36950 |
| | Fascin | 86 | 2 | 7.02 | 54992 |
| | Tubulin beta-2 chain | 85 | 5 | 4.64 | 50095 |
| | Chloride intracellular channel protein 1 | 79 | 12 | 4.94 | 27117 |
| | Multifunctional protein ADE2 | 74 | 2 | 8.7 | 50389 |
| | OTTHUMP00000021786 | 69 | 1 | 4.7 | 55459 |
| | Transketolase | 68 | 2 | 8.54 | 68519 |
| | 14-3-3 protein zeta/delta | 64 | 4 | 4.57 | 27899 |
| | Alpha-actinin-1 | 62 | 2 | 5.13 | 103563 |
| | ubiquitin and ribosomal protein S27a precursor | 62 | 8 | 10.4 | 18296 |
| | Pyruvate dehydrogenase E1 component alpha subuni | 62 | 3 | 9.26 | 43952 |
| | poly(rC)-binding protein 2 isoform b | 60 | 3 | 6.37 | 38597 |
| | Elongation factor 1-gamma | 60 | 3 | 6.26 | 50298 |
| | PREDICTED: similar to peptidylprolyl isomerase A | 55 | 4 | 9.87 | 24693 |
| | Transportin-1 | 55 | 1 | 4.69 | 103771 |
| | Nucleoside diphosphate kinase A | 55 | 9 | 5.78 | 17309 |
| | 6-phosphogluconate dehydrogenase, decarboxylatin | 54 | 3 | 6.98 | 53488 |
| | Heat shock 70 kDa protein 4 | 52 | 2 | 5.03 | 95096 |
| | Small glutamine-rich tetratricopeptide repeat-co | 52 | 4 | 4.64 | 34270 |
| | Alpha-actinin-4 | 51 | 2 | 5.16 | 105245 |
| | heterogeneous nuclear ribonucleoprotein A1 isofo | 50 | 2 | 9.58 | 38837 |
| | Brain acid soluble protein 1 | 50 | 15 | 4.47 | 22549 |
| | Importin beta-1 subunit | 49 | 1 | 4.53 | 98420 |
| | Isoform 1 of Nuclear autoantigenic sperm protein | 48 | 1 | 4.11 | 85471 |
| | Heat shock protein 60 | 48 | 2 | 5.59 | 61346 |
| | Isoform 1 of Serpin B13 | 45 | 3 | 5.39 | 44305 |
| | 116 kDa U5 small nuclear ribonucleoprotein compo | 45 | 1 | 4.7 | 110336 |
| | T-complex protein 1 subunit beta | 43 | 1 | 6 | 57663 |
| | hypothetical protein LOC64423 isoform 1 | 42 | 2 | 5.61 | 78284 |
| | Protein S100-A11 | 42 | 8 | 7.52 | 11847 |
| | UV excision repair protein RAD23 homolog B | 41 | 2 | 4.63 | 43202 |
| | hematological and neurological expressed 1 isofo | 41 | 9 | 5.35 | 16005 |
| | PREDICTED: similar to ribosomal protein S3a isof | 41 | 5 | 9.87 | 25033 |
| 55 | Isoform 1 of Heat shock cognate 71 kDa protein | 168 | 6 | 5.2 | 71082 |
| | Hypothetical protein DKFZp761K0511 | 135 | 3 | 5.13 | 85189 |
| | Peroxiredoxin-1 | 106 | 10 | 9.22 | 22324 |
| | Heat shock 70 kDa protein 1 | 81 | 2 | 5.36 | 70294 |
| | Isoform 1 of Carbamoyl-phosphate synthase [ammon | 75 | 1 | 6.3 | 165975 |
| | 14-3-3 protein theta | 64 | 4 | 4.53 | 28032 |
| | T-complex protein 1 subunit delta | 60 | 2 | 9.08 | 58270 |
| | Methylosome protein 50 | 56 | 4 | 4.88 | 37442 |
| | Heat shock protein 60 | 55 | 2 | 5.59 | 61346 |
| | tyrosine 3-monooxygenase/tryptophan 5-monooxygen | 54 | 4 | 4.61 | 28179 |
| | Elongation factor 2 | 52 | 1 | 6.42 | 96115 |
| | Endoplasmin precursor | 51 | 1 | 4.61 | 92696 |
| | lactate dehydrogenase A | 51 | 3 | 9.26 | 36950 |
| | GTP-binding nuclear protein Ran | 51 | 4 | 7.84 | 24448 |
| | Plastin-1 | 50 | 2 | 5.21 | 70707 |
| | Isoform Long of Trifunctional purine biosyntheti | 49 | 1 | 6.27 | 108953 |
| | Triosephosphate isomerase | 48 | 4 | 5.4 | 30802 |
| | 14-3-3 protein zeta/delta | 47 | 4 | 4.57 | 27899 |
| | enolase 1 | 46 | 2 | 7.71 | 47481 |

TABLE 4-continued

Protein identification by LC-MS/MS after free-flow isoelectric focusing without PPS

| Fraction | Peptide | Mascot Score | MS Coverage | pI-Value | Protein MW |
|---|---|---|---|---|---|
| | Stress-70 protein, mitochondrial precursor | 44 | 2 | 5.81 | 73920 |
| | PREDICTED: similar to Elongation factor 1-gamma | 43 | 3 | 5.27 | 36636 |
| | Transcription elongation factor A protein 2 | 41 | 4 | 10.39 | 34206 |
| | Isoform 1 of Signal transducer and activator of | 39 | 1 | 5.9 | 89190 |

TABLE 5

Protein identification by LC MS/MS after free-flow isoelectric focusing with PPS

| Fraction | Title | Mascot Score | MS Coverage | pI-Value | Protein MW |
|---|---|---|---|---|---|
| 32 | pyruvate kinase 3 isoform 1 | 405 | 18 | 9 | 58470 |
| | Fatty acid synthase | 325 | 3 | 5.98 | 275850 |
| | Vimentin | 248 | 10 | 4.91 | 53545 |
| | Actin, aortic smooth muscle | 223 | 10 | 5.12 | 42381 |
| | Phosphoglycerate kinase 1 | 192 | 8 | 9.21 | 44854 |
| | Fructose-bisphosphate aldolase A | 190 | 7 | 9.24 | 39720 |
| | enolase 1 | 154 | 9 | 7.71 | 47481 |
| | Hypothetical protein | 146 | 3 | 4.92 | 72492 |
| | Brain acid soluble protein 1 | 131 | 29 | 4.47 | 22549 |
| | Tubulin beta-2C chain | 126 | 4 | 4.65 | 50255 |
| | Asparagine synthetase | 123 | 5 | 6.41 | 64768 |
| | Isoform 1 of Carbamoyl-phosphate synthase [ammon | 122 | 1 | 6.3 | 165975 |
| | L-lactate dehydrogenase B chain | 115 | 7 | 5.66 | 36769 |
| | T-complex protein 1 subunit beta | 114 | 5 | 6 | 57663 |
| | CDNA FLJ45525 fis, clone BRTHA2026311, highly si | 111 | 2 | 5.04 | 54408 |
| | Hypothetical protein DKFZp761K0511 | 108 | 4 | 5.13 | 85189 |
| | Isoform 2 of Heterogeneous nuclear ribonucleopro | 102 | 7 | 6.58 | 36059 |
| | Transgelin-2 | 101 | 13 | 9.41 | 22417 |
| | Isoform 1 of Sequestosome-1 | 100 | 12 | 5.12 | 48638 |
| | Transketolase | 97 | 4 | 8.54 | 68519 |
| | Peroxiredoxin-6 | 95 | 8 | 5.98 | 25002 |
| | Phosphatidylethanolamine-binding protein 1 | 94 | 9 | 7.84 | 21027 |
| | heterogeneous nuclear ribonucleoprotein H1 | 89 | 3 | 5.87 | 49484 |
| | T-complex protein 1 subunit epsilon | 86 | 1 | 5.34 | 60089 |
| | Tu translation elongation factor, mitochondrial | 86 | 2 | 7.92 | 50185 |
| | T-complex protein 1 subunit delta | 86 | 2 | 9.08 | 58270 |
| | Signal recognition particle 14 kDa protein | 85 | 10 | 10.64 | 14649 |
| | Heat shock 70 kDa protein 1 | 85 | 5 | 5.36 | 70294 |
| | Rab GDP dissociation inhibitor beta | 84 | 2 | 6.08 | 51087 |
| | tyrosine 3-monooxygenase/tryptophan 5-monooxygen | 81 | 5 | 4.61 | 28179 |
| | Peroxiredoxin-2 | 80 | 8 | 5.59 | 21918 |
| | Ubiquitin-activating enzyme E1 | 76 | 1 | 5.41 | 118858 |
| | PREDICTED: similar to Heat shock protein HSP 90- | 75 | 5 | 5.37 | 22588 |
| | 14-3-3 protein sigma | 74 | 5 | 4.53 | 27871 |
| | T-complex protein 1 subunit zeta | 74 | 2 | 6.24 | 58313 |
| | Heterogeneous nuclear ribonucleoprotein R | 71 | 2 | 8.8 | 71184 |
| | Reticulocalbin-1 precursor | 70 | 3 | 4.72 | 38866 |
| | Hydroxymethylglutaryl-CoA synthase, cytoplasmic | 70 | 3 | 5.09 | 57828 |
| | Isoform 1 of Proteasome activator complex subuni | 69 | 5 | 5.61 | 29602 |
| | lactate dehydrogenase A | 64 | 3 | 9.26 | 36950 |
| | 14-3-3 protein epsilon | 63 | 4 | 4.48 | 29326 |
| | 60S acidic ribosomal protein P2 | 62 | 10 | 4.22 | 11658 |
| | Programmed cell death 5 short isoform | 60 | 32 | 4.77 | 4472 |
| | 46 kDa protein | 60 | 4 | 4.63 | 46713 |
| | Protein S100-A6 | 59 | 8 | 5.21 | 10230 |
| | Cytokeratin type II | 59 | 1 | 8.66 | 59753 |
| | PREDICTED: similar to Phosphoglycerate mutase 1 | 56 | 7 | 6.82 | 29003 |
| | Transitional endoplasmic reticulum ATPase | 56 | 1 | 5 | 89819 |
| | Stress-induced-phosphoprotein 1 | 54 | 2 | 6.42 | 63227 |
| | Isoform 2 of Nucleophosmin | 53 | 3 | 4.32 | 29617 |
| | Protein farnesyltransferase/geranylgeranyltransf | 52 | 3 | 4.82 | 44495 |
| | TALDO1 protein | 50 | 3 | 9.7 | 35535 |
| | Alpha-actinin-4 | 49 | 1 | 5.16 | 105245 |
| | Thioredoxin domain-containing protein 4 precurso | 49 | 2 | 4.96 | 47341 |
| | Peptidyl-prolyl cis-trans isomerase A | 49 | 13 | 9.14 | 18098 |
| | Beta-enolase | 48 | 6 | 8.68 | 47168 |
| | Isoform 1 of Nicotinamide phosphoribosyltransfer | 48 | 3 | 6.78 | 55772 |
| | ISOFORM 1 OF NICOTINAMIDE | 46 | 0 | 5.66 | 0 |

TABLE 5-continued

Protein identification by LC MS/MS after free-flow isoelectric focusing with PPS

| Fraction | Title | Mascot Score | MS Coverage | pI-Value | Protein MW |
|---|---|---|---|---|---|
| | PHOSPHORIBOSYLTRANSFE | | | | |
| | 12 kDa protein | 45 | 7 | 5.22 | 12680 |
| | Transportin-1 | 43 | 1 | 4.69 | 103771 |
| | myosin, light polypeptide 6, alkali, smooth musc | 42 | 9 | 4.41 | 17090 |
| | Similar to annexin A2 isoform 1 | 41 | 5 | 6.58 | 38806 |
| | chaperonin containing TCP1, subunit 3 isoform b | 41 | 4 | 6.08 | 60994 |
| | E(Y)2 homolog | 41 | 16 | 10.16 | 11635 |
| | Isoform 1 of Heterogeneous nuclear ribonucleopro | 40 | 2 | 9.15 | 69788 |
| | tropomyosin 1 alpha chain isoform 2 | 40 | 4 | 4.55 | 32715 |
| | Annexin A1 | 40 | 3 | 6.68 | 38787 |
| | Annexin A3 | 39 | 3 | 5.55 | 36393 |
| | Malate dehydrogenase, cytoplasmic | 39 | 5 | 7.66 | 36500 |
| | Peroxiredoxin-1 | 38 | 3 | 9.22 | 22324 |
| 39 | heat shock 70 kDa protein 1A | 357 | 10 | 5.4 | 70280 |
| | Hypothetical protein DKFZp761K0511 | 261 | 10 | 5.13 | 85189 |
| | Stress-70 protein, mitochondrial precursor | 254 | 7 | 5.81 | 73920 |
| | Hypothetical protein | 247 | 6 | 4.92 | 72492 |
| | Isoform 1 of Heat shock cognate 71 kDa protein | 240 | 7 | 5.24 | 71082 |
| | Filamin A, alpha | 208 | 1 | 5.64 | 282581 |
| | Heat shock protein 60 | 202 | 7 | 5.59 | 61346 |
| | Heat shock protein HSP 90-alpha 2 | 179 | 3 | 4.95 | 98622 |
| | Heat-shock protein beta-1 | 156 | 22 | 5.97 | 22826 |
| | Cofilin-1 | 149 | 15 | 9.19 | 18588 |
| | Chloride intracellular channel protein 1 | 147 | 12 | 4.94 | 27117 |
| | Actin, cytoplasmic 1 | 147 | 11 | 5.18 | 42052 |
| | eukaryotic translation initiation factor 4B | 134 | 5 | 5.41 | 69167 |
| | enolase 1 | 126 | 5 | 7.71 | 47481 |
| | Fructose-bisphosphate aldolase A | 120 | 11 | 9.24 | 39720 |
| | Protein disulfide-isomerase A3 precursor | 118 | 4 | 5.95 | 57146 |
| | Similar to annexin A2 isoform 1 | 117 | 6 | 6.58 | 38806 |
| | Vimentin | 112 | 4 | 4.91 | 53545 |
| | Phosphatidylethanolamine-binding protein 1 | 111 | 10 | 7.84 | 21027 |
| | T-complex protein 1 subunit theta | 108 | 4 | 5.31 | 60311 |
| | Brain acid soluble protein 1 | 100 | 15 | 4.47 | 22549 |
| | Annexin A1 | 99 | 4 | 6.68 | 38787 |
| | lactate dehydrogenase A | 98 | 8 | 9.26 | 36950 |
| | 40 kDa protein | 95 | 7 | 4.58 | 39893 |
| | Glucose-6-phosphate isomerase | 95 | 2 | 9.14 | 63204 |
| | Electron transfer flavoprotein alpha-subunit, mi | 95 | 5 | 9.47 | 35400 |
| | Tubulin beta-2 chain | 91 | 5 | 4.64 | 50095 |
| | Glyceraldehyde-3-phosphate dehydrogenase | 91 | 4 | 9.3 | 36070 |
| | Fascin | 90 | 2 | 7.02 | 54992 |
| | Fatty acid synthase | 86 | 1 | 5.98 | 275850 |
| | Proteasome subunit beta type 6 precursor | 85 | 4 | 4.65 | 25570 |
| | Stathmin-2 | 85 | 10 | 9.21 | 20929 |
| | 6-phosphogluconate dehydrogenase, decarboxylatin | 83 | 3 | 6.98 | 53488 |
| | Isoform 1 of Carbamoyl-phosphate synthase [ammon | 80 | 0 | 6.3 | 165975 |
| | 130 kDa leucine-rich protein | 80 | 1 | 5.86 | 160023 |
| | Actin, aortic smooth muscle | 77 | 6 | 5.12 | 42381 |
| | Calmodulin | 75 | 10 | 3.93 | 16696 |
| | PREDICTED: similar to peptidylprolyl isomerase A | 75 | 4 | 9.87 | 24693 |
| | 14-3-3 protein zeta/delta | 74 | 4 | 4.57 | 27899 |
| | Isoform Long of Trifunctional purine biosyntheti | 74 | 2 | 6.27 | 108953 |
| | Tubulin beta-2C chain | 73 | 5 | 4.65 | 50255 |
| | Alpha-actinin-4 | 72 | 1 | 5.16 | 105245 |
| | Protein S100-A11 | 72 | 8 | 7.52 | 11847 |
| | RcTPI1 (Fragment) | 69 | 5 | 9.24 | 27211 |
| | Isoform M1 of Pyruvate kinase isozymes M1/M2 | 69 | 3 | 8.64 | 58407 |
| | Phosphoglycerate kinase 1 | 69 | 4 | 9.21 | 44854 |
| | Elongation factor 1-delta | 68 | 4 | 4.75 | 31086 |
| | Thioredoxin-like protein 5 | 67 | 11 | 5.27 | 14217 |
| | Nascent polypeptide-associated complex alpha sub | 66 | 6 | 4.36 | 23370 |
| | Ubiquitin-activating enzyme E1 | 65 | 2 | 5.8 | 57443 |
| | Pyruvate dehydrogenase E1 component alpha subuni | 64 | 3 | 9.26 | 43952 |
| | ATP-citrate synthase | 62 | 1 | 7.08 | 121660 |
| | 50 kDa protein | 60 | 5 | 4.61 | 50168 |
| | Tryptophanyl-tRNA synthetase | 60 | 2 | 5.8 | 53474 |
| | Heat shock 70 kDa protein 4 | 59 | 2 | 5.03 | 95096 |
| | Elongation factor 1-gamma | 59 | 3 | 6.26 | 50298 |
| | Isoform 1 of Transcription intermediary factor 1 | 59 | 2 | 5.44 | 90261 |
| | Multifunctional protein ADE2 | 58 | 2 | 8.7 | 50389 |
| | L-lactate dehydrogenase B chain | 57 | 3 | 5.66 | 36769 |
| | hematological and neurological expressed 1 isofo | 57 | 9 | 5.35 | 16005 |
| | Transketolase | 56 | 2 | 8.54 | 68519 |
| | Isoform 1 of Heterogeneous nuclear ribonucleopro | 55 | 2 | 5.26 | 51230 |

TABLE 5-continued

Protein identification by LC MS/MS after free-flow isoelectric focusing with PPS

| Fraction | Title | Mascot Score | MS Coverage | pI-Value | Protein MW |
|---|---|---|---|---|---|
| | GMP synthase | 54 | 1 | 6.44 | 77408 |
| | Esterase D | 53 | 4 | 6.62 | 31956 |
| | Importin beta-1 subunit | 52 | 1 | 4.53 | 98420 |
| | S-adenosylmethionine synthetase isoform type-2 | 51 | 3 | 6.02 | 43975 |
| | poly(rC)-binding protein 2 isoform b | 51 | 3 | 6.37 | 38597 |
| | Isoform 1 of Nuclear autoantigenic sperm protein | 51 | 1 | 4.11 | 85471 |
| | Nucleoside diphosphate kinase A | 51 | 9 | 5.78 | 17309 |
| | CDNA FLJ45525 fis, clone BRTHA2026311, highly si | 49 | 2 | 5.04 | 54408 |
| | Histone H4 | 47 | 9 | 11.85 | 11229 |
| | Small glutamine-rich tetratricopeptide repeat-co | 46 | 4 | 4.64 | 34270 |
| | T-complex protein 1 subunit beta | 46 | 1 | 6 | 57663 |
| | Myosin-11 | 45 | 0 | 5.29 | 228054 |
| | 40S ribosomal protein S13 | 45 | 8 | 10.96 | 17081 |
| | 116 kDa U5 small nuclear ribonucleoprotein compo | 43 | 1 | 4.7 | 110336 |
| | Thioredoxin-like protein 2 | 42 | 3 | 5.19 | 37693 |
| | Transportin-1 | 41 | 1 | 4.69 | 103771 |
| | Thymosin beta-10 | 41 | 18 | 5.16 | 4892 |
| | Proteasome subunit beta type 3 | 40 | 7 | 6.17 | 23219 |
| 47 | Phosphoglycerate kinase 1 | 261 | 10 | 9.2 | 44854 |
| | Heat shock 70 kDa protein 1 | 246 | 5 | 5.36 | 70294 |
| | Hypothetical protein DKFZp761K0511 | 202 | 9 | 5.13 | 85189 |
| | Isoform 2 of L-lactate dehydrogenase A chain | 199 | 12 | 9.11 | 36953 |
| | Tubulin alpha-ubiquitous chain | 195 | 12 | 4.81 | 50804 |
| | Heat shock protein 60 | 188 | 5 | 5.59 | 61346 |
| | Tubulin beta-2 chain | 182 | 10 | 4.64 | 50095 |
| | Tubulin beta-2C chain | 176 | 10 | 4.65 | 50255 |
| | Glyceraldehyde-3-phosphate dehydrogenase | 167 | 9 | 9.3 | 36070 |
| | L-lactate dehydrogenase B chain | 155 | 7 | 5.66 | 36769 |
| | Triosephosphate isomerase | 147 | 13 | 5.4 | 30802 |
| | enolase 1 | 129 | 5 | 7.71 | 47481 |
| | Isoform 1 of Heat shock cognate 71 kDa protein | 128 | 4 | 5.24 | 71082 |
| | Peroxiredoxin-1 | 126 | 15 | 9.22 | 22324 |
| | Actin, cytoplasmic 1 | 114 | 7 | 5.18 | 42052 |
| | Isoform 1 of Carbamoyl-phosphate synthase [ammon | 104 | 2 | 6.3 | 165975 |
| | Nucleoside diphosphate kinase B | 95 | 12 | 9.35 | 17401 |
| | Heat shock protein HSP 90-alpha 2 | 94 | 3 | 4.95 | 98622 |
| | PREDICTED: similar to Pyruvate kinase, isozymes | 80 | 6 | 6.56 | 39895 |
| | Protein S100-A11 | 78 | 19 | 7.52 | 11847 |
| | PREDICTED: similar to SMT3 suppressor of mif two | 78 | 7 | 5.92 | 18200 |
| | Proliferating cell nuclear antigen | 77 | 4 | 4.42 | 29092 |
| | Heat-shock protein beta-1 | 70 | 4 | 5.97 | 22826 |
| | Protein S100-P | 69 | 13 | 4.6 | 10450 |
| | Elongation factor 2 | 69 | 2 | 6.42 | 96115 |
| | Annexin A1 | 66 | 4 | 6.68 | 38787 |
| | Fatty acid synthase | 58 | 0 | 5.98 | 275850 |
| | GTP-binding nuclear protein Ran | 57 | 10 | 7.84 | 24448 |
| | Eukaryotic initiation factor 4A-I | 57 | 2 | 5.19 | 46353 |
| | Adenosylhomocysteinase | 54 | 4 | 5.91 | 48124 |
| | Profilin-1 | 53 | 11 | 9.45 | 15085 |
| | Peptidyl-prolyl cis-trans isomerase A | 48 | 7 | 9.14 | 18098 |
| | T-complex protein 1 subunit theta | 45 | 2 | 5.31 | 60311 |
| | Protein disulfide-isomerase A3 precursor | 44 | 2 | 5.95 | 57146 |
| 56 | Hsp89-alpha-delta-N | 186 | 4 | 4.9 | 63839 |
| | Hypothetical protein DKFZp761K0511 | 153 | 3 | 5.13 | 85189 |
| | heterogeneous nuclear ribonucleoprotein F | 111 | 3 | 5.27 | 45985 |
| | S-adenosylmethionine synthetase isoform type-2 | 94 | 3 | 6.02 | 43975 |
| | 26S proteasome non-ATPase regulatory subunit 3 | 93 | 2 | 9.01 | 61054 |
| | Protein disulfide-isomerase precursor | 75 | 3 | 4.61 | 57480 |
| | PREDICTED: similar to Phosphoglycerate mutase 1 | 71 | 4 | 6.82 | 29003 |
| | heterogeneous nuclear ribonucleoprotein H1 | 66 | 3 | 5.87 | 49484 |
| | ATP synthase alpha chain, mitochondrial precurso | 66 | 1 | 9.61 | 59828 |
| | Isoform Mitochondrial of Peroxiredoxin-5, mitoch | 64 | 6 | 9.93 | 22298 |
| | T-complex protein 1 subunit theta | 63 | 2 | 5.31 | 60311 |
| | Reticulocalbin-1 precursor | 62 | 4 | 4.72 | 38866 |
| | Calreticulin precursor | 48 | 3 | 4.14 | 48283 |
| | Proliferation-associated protein 2G4 | 48 | 3 | 6.12 | 43970 |
| | SHC (Src homology 2 domain containing) transform | 42 | 2 | 5.99 | 63367 |
| | L-aminoadipate-semialdehyde dehydrogenase-phosph | 42 | 4 | 6.39 | 35981 |

The invention claimed is:

1. A method for separating analytes in a sample by free-flow electrophoresis, comprising performing a free-flow electrophoretic (FFE) separation including at least one MS-compatible zwitterionic or nonionic surfactant,
   wherein said at least one MS-compatible zwitterionic or nonionic surfactant is a cleavable surfactant capable of being cleaved into at least two moieties, and wherein cleavage of the cleavable surfactant is carried out after FFE separation.

2. The method according to claim 1, wherein at least part of the sample is collected in one or more than one fractions after the electrophoretic separation.

3. The method according to claim 1, wherein said at least one MS-compatible zwitterionic or nonionic surfactant is comprised in at least one medium selected from the group consisting of a sample medium, a separation medium, and combinations thereof.

4. The method according to claim 1, wherein the operation modus of the free-flow electrophoresis is selected from the group consisting of continuous mode, static interval mode, and cyclic interval mode.

5. The method according to claim 1, wherein the separation is carried out by a separation mode selected from the group consisting of free-flow isoelectric focusing (FF-IEF), free-flow zone electrophoresis (FF-ZE), and free-flow isotachophoresis (FF-ITP).

6. The method according to claim 1, wherein said cleavable surfactant is acid labile, base labile, chemo reactive or photo labile.

7. The method according to claim 1, wherein the cleavable surfactant is selected from the group consisting of {2-[(dimethyl-octyl-silanyl)-ethoxy]-2hydroxy-ethyl}-trimethyl ammonium bromide, 3-(2,4,6-trihydroxyphenyl)acryl acid octyl ester and 3-[3-(I,I-bisalkoxyethyl)pyridine-l-yl]propane-l-sulfonate.

8. The method according to claim 1, wherein at least one of the moieties of a cleaved zwitterionic or nonionic surfactant can be removed by centrifugation, evaporation, filtration, or a combination thereof.

9. The method according to claim 1, wherein cleavage of the cleavable surfactant is carried out by acidifying at least one fraction comprising an acid labile cleavable surfactant, alkalifying at least one fraction comprising a base labile cleavable surfactant, subjecting at least one fraction to irradiation comprising a photo labile cleavable surfactant, or adding a reagent to at least one fraction that is capable of breaking a bond within a chemo reactive surfactant.

10. The method according to claim 9, wherein said reagent is fluoride.

11. The method according to claim 1, wherein at least part of a sample is subjected to a protein digestion step.

12. The method according to claim 1, further comprising analyzing at least a part of a fraction obtained from the free-flow electrophoretic separation.

13. The method according to claim 12, wherein the step of analyzing the part of the fraction is performed by free-flow electrophoresis, gel electrophoresis, ID- and 2D-PAGE, MS, MALDI MS, ESI MS, SELDI MS, LCMS(/MS), MALDI-TOF-MS(/MS), IR-spectroscopy, UV spectroscopy, ELISA, HPLC, Edman sequencing, NMR spectroscopy, surface plasmon resonance, X-ray diffraction, nucleic acid sequencing, electroblotting, amino acid sequencing, flow cytometry, circular dichroism, or any combination thereof.

14. The method according to claim 1, wherein the analytes are selected from the group consisting of organic molecules, inorganic molecules, bioparticles, biopolymers, biomolecules, and any combination thereof.

15. The method according to claim 14, wherein said analytes are proteins.

16. The method according to claim 15, wherein the proteins are selected from the group consisting of membrane associated proteins, integral membrane proteins, lipophilic proteins, protein aggregates, protein complexes, peptides, hydrophobic peptides, DNA-protein complexes, DNA, membranes, membrane fragments, hormones, liposomes, virus particles, antibodies, antibody complexes, and combinations thereof.

17. The method according to claim 15, wherein the analytes are selected from the group consisting of lipids, saccharides, saccharide derivatives, polysaccharides, polysaccharide derivatives, dextranes, nanoparticles, constituents of plastic, latex paint particles, polystyrenes, polymethylmethacrylates, cellulose derivatives, polyacids, pharmaceutical drugs, prodrugs, a metabolite of a drug explosives, toxins, carcinogens, poisons, allergens, infectious agents, and combinations thereof.

18. The method according to claim 1, wherein a counter flow medium comprising a cleaving agent comes in contact with or is mixed with at least part of a fraction of a sample after free-flow electrophoretic separation that comprises a cleavable surfactant.

19. The method according to claim 1, wherein a counter flow medium is used to adapt media conditions so as to stabilize a cleavable surfactant comprised therein after the free-flow electrophoretic separation.

20. A free-flow electrophoresis separation medium, comprising at least one MS-compatible zwitterionic or nonionic surfactant, wherein said separation medium is selected from the group consisting of A/B separation media, volatile media and complementary multi pair buffer media.

21. A free-flow electrophoresis kit comprising at least one separation medium and at least one MS-compatible zwitterionic or nonionic surfactant, wherein said separation medium is selected from the group consisting of A/B separation media, volatile media, and complementary multi pair buffer media.

22. The kit according to claim 21, wherein the at least one MS-compatible zwitterionic or nonionic surfactant is a cleavable surfactant.

23. The kit according to claim 22, further comprising an agent for cleaving said at least one cleavable surfactant.

24. The kit according to claim 21, further comprising an anodic stabilizing medium, or a cathodic stabilizing medium, or a combination thereof.

25. The kit according to claim 21, further comprising at least one focus medium.

26. The kit according to claim 21, wherein components of the kit are present as aqueous solutions ready for use in a free-flow electrophoresis method.

27. The kit according to claim 21, wherein components of the kit are present as concentrated aqueous stock solutions that are to be diluted to the appropriate concentration for use in a free-flow electrophoresis method.

28. The kit according to claim 21, wherein components of the kit are present in dried or lyophilized form that are to be dissolved with solvent, preferably water, to the appropriate concentration for use in a free-flow electrophoresis method.

29. The kit according to claim 21, further comprising a product manual that describes one or more experimental protocols, and optionally storage conditions for the components.

* * * * *

UNITED STATES PATENT AND TRADEMARK OFFICE
CERTIFICATE OF CORRECTION

PATENT NO. : 8,449,744 B2  
APPLICATION NO. : 12/742306  
DATED : May 28, 2013  
INVENTOR(S) : Mikkel Nissum Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 514 days.

Signed and Sealed this

Eighth Day of September, 2015

Michelle K. Lee
*Director of the United States Patent and Trademark Office*